(12) United States Patent
Maeda et al.

(10) Patent No.: US 7,916,929 B2
(45) Date of Patent: *Mar. 29, 2011

(54) DEFECT INSPECTION METHOD AND APPARATUS

(75) Inventors: Shunji Maeda, Yokohama (JP); Kenji Oka, Yokohama (JP); Yukihiro Shibata, Fujisawa (JP); Minoru Yoshida, Yokohama (JP); Chie Shishido, Yokohama (JP); Yuji Takagi, Kamakura (JP); Atsushi Yoshida, Yokohama (JP); Kazuo Yamaguchi, Sagamihara (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/359,452

(22) Filed: Jan. 26, 2009

(65) Prior Publication Data

US 2009/0214102 A1 Aug. 27, 2009

Related U.S. Application Data

(63) Continuation of application No. 11/858,215, filed on Sep. 20, 2007, now Pat. No. 7,512,259, which is a continuation of application No. 11/204,181, filed on Aug. 16, 2005, now Pat. No. 7,274,813, which is a continuation of application No. 09/294,137, filed on Apr. 20, 1999, now Pat. No. 6,947,587.

(30) Foreign Application Priority Data

Apr. 21, 1998 (JP) .................................. 10-110383
Sep. 18, 1998 (JP) .................................. 10-264275

(51) Int. Cl.
*G06K 9/00* (2006.01)

(52) U.S. Cl. ....................................... 382/141; 382/145

(58) Field of Classification Search .................. 382/141, 382/145, 149

See application file for complete search history.

(56) References Cited

U.S. PATENT DOCUMENTS

| | | | |
|---|---|---|---|
| 4,633,504 A | 12/1986 | Wihl | |
| 4,669,123 A | 5/1987 | Kobayashi et al. | |
| 4,791,586 A | 12/1988 | Maeda et al. | |
| 4,805,123 A | 2/1989 | Specht et al. | |
| 4,926,489 A | 5/1990 | Danielson et al. | |
| 5,153,444 A | 10/1992 | Maeda et al. | |
| 5,204,910 A | 4/1993 | Lebeau | |

(Continued)

FOREIGN PATENT DOCUMENTS

JP 55-74409 6/1980

(Continued)

*Primary Examiner* — Tom Y Lu

(74) *Attorney, Agent, or Firm* — Antonelli, Terry, Stout & Kraus, LLP.

(57) ABSTRACT

A method of inspecting patterns, including: adjusting a brightness of at least one of a first bright field image and a second bright field image detected from a specimen and directed to similar patterns on differing parts of the specimen, so as to more closely match a brightness; comparing the images which are adjusted in brightness to match with each other to detect dissimilarities indicative of a defect of the pattern, wherein in adjusting the brightness, the brightness between the first bright field image and the second bright field image is adjusted by performing a gradation conversion of at least one of the brightness between the first bright field image and the second bright field image; and wherein in the comparing, said defect of the pattern is detected by using information of a scattered diagram of brightness of the first bright field image and the second bright field image.

16 Claims, 39 Drawing Sheets

U.S. PATENT DOCUMENTS

| | | |
|---|---|---|
| 5,640,200 A | 6/1997 | Michael |
| 5,659,172 A | 8/1997 | Wagner et al. |
| 5,699,447 A * | 12/1997 | Alumot et al. ............... 382/145 |
| 5,808,735 A | 9/1998 | Lee et al. |
| 5,949,901 A | 9/1999 | Nichani et al. |
| 5,963,314 A | 10/1999 | Worster et al. |
| 6,067,153 A | 5/2000 | Mizuno |
| 6,111,596 A | 8/2000 | Haskell et al. |
| 6,118,525 A | 9/2000 | Fossey et al. |
| 6,128,108 A | 10/2000 | Teo |
| 6,133,576 A | 10/2000 | Shafer et al. |
| 6,181,805 B1 | 1/2001 | Koike et al. |
| 6,282,309 B1 | 8/2001 | Emery |
| 6,504,948 B1 | 1/2003 | Schemmel et al. |

FOREIGN PATENT DOCUMENTS

| | | |
|---|---|---|
| JP | 61-212708 | 9/1986 |
| JP | 04-194702 | 7/1992 |
| JP | 06-174652 | 6/1994 |
| JP | 07-153804 | 6/1995 |
| JP | 8-10463 | 1/1996 |
| JP | 9-312318 | 12/1997 |

* cited by examiner

- 20 MEMORY CHIP
- 22 PERIPHERAL CIRCUITS
- 21 MEMORY MAT

FIG. 5
PRIOR ART

|     | −1 | 0 | 1 |
|---|---|---|---|
| −1 | $8.28 \times 10^{11}$ | $1.56 \times 10^{11}$ | $9.07 \times 10^{11}$ |
| 0  | $8.55 \times 10^{11}$ | 0 | $8.59 \times 10^{11}$ |
| 1  | $9.0 \times 10^{11}$ | $1.55 \times 10^{11}$ | $8.33 \times 10^{11}$ |

FIG. 6
PRIOR ART

|     | −1 | 0 | 1 |
|---|---|---|---|
| −1 | 967323 | 742941 | 951727 |
| 0  | 953922 | 732608 | 939418 |
| 1  | 950797 | 728523 | 937704 |

$$F = \begin{bmatrix} 1-\alpha-\beta & \alpha \\ \beta & 0 \end{bmatrix}$$

$$F' = \begin{bmatrix} 0 & \beta \\ \alpha & 1-\alpha-\beta \end{bmatrix}$$

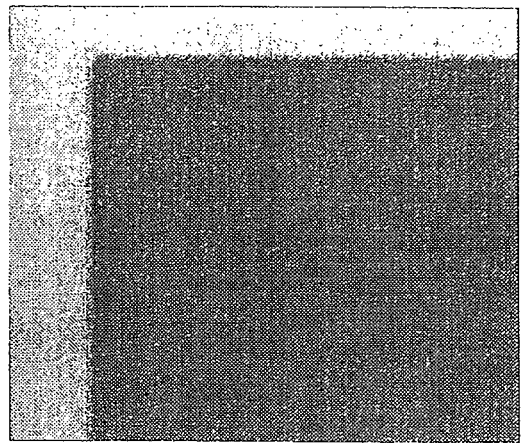
$f(x, y)$  FIG. 13A
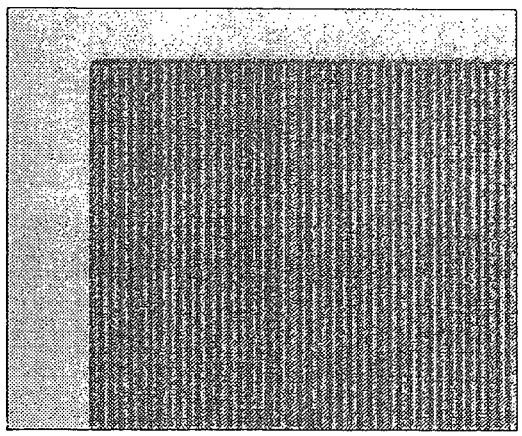
$g(x, y)$  FIG. 13B
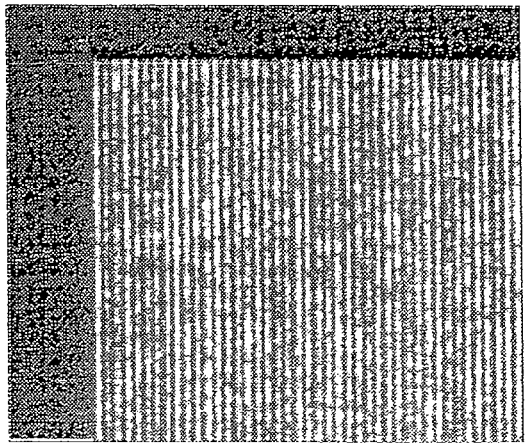
$|f(x, y) - g(x, y)|$  FIG. 13C
DIFFERENCE IMAGE g(x, y)

BRIGHTNESS HISTOGRAM OF g(x, y)

f(x, y)

$\mu 1 = 120$   $\mu 2 = 160$

BRIGHTNESS HISTOGRAM OF f(x, y)

a * g(x, y)+b

BRIGHTNESS HISTOGRAM OF {a * g(x, y)+b}

* a,b ARE ESTIMATED WITHIN LOCAL
REGION OF IMAGE AT EACH POINT

DIFFERENCE IMAGE 1 (3×3)

DIFFERENCE IMAGE 2 (5×5)

DIFFERENCE IMAGE 3 (7×7)

DIFFERENCE IMAGE 4 (7×7, WEIGHTED)

FIG. 21
1) AFTER ALIGNMENT WITH
   ACCURACY OF PIXEL UNIT
| GRADIENT | INTERCEPT |
|---|---|
| 1.038 | 2.336 |
$V_r$ = 125.774
$V_e$ = 59.653
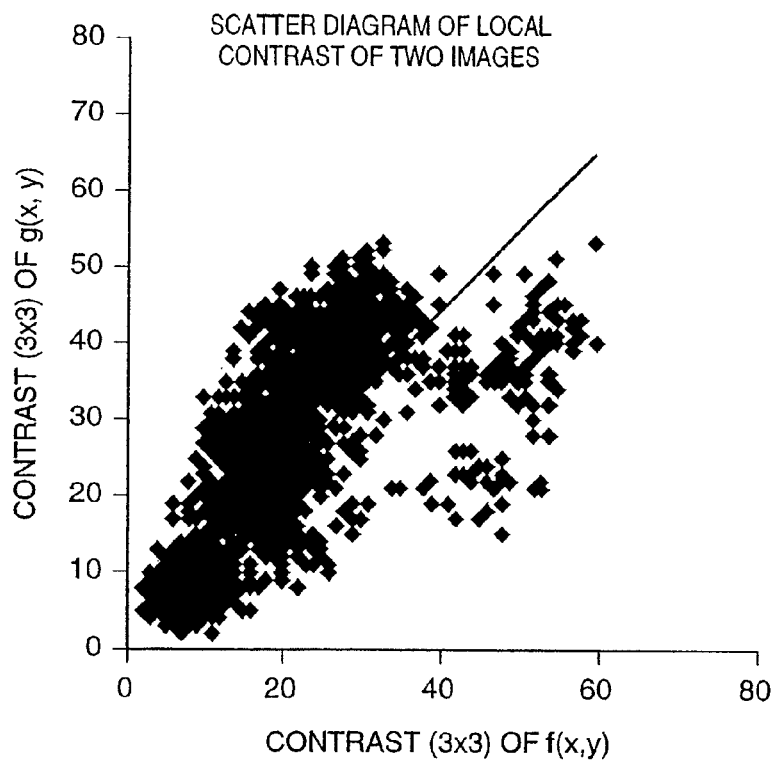
VALUE OF $V_e$
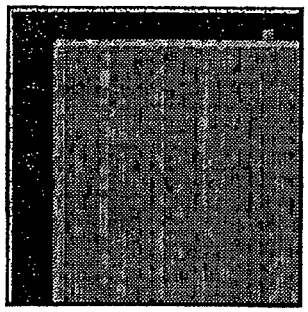

FIG. 22
2) AFTER MATCHING OF BRIGHTNESS
| GRADIENT | INTERCEPT |
|---|---|
| 0.958 | −1.649 |
$V_r$ = 175.852
$V_e$ = 9.603
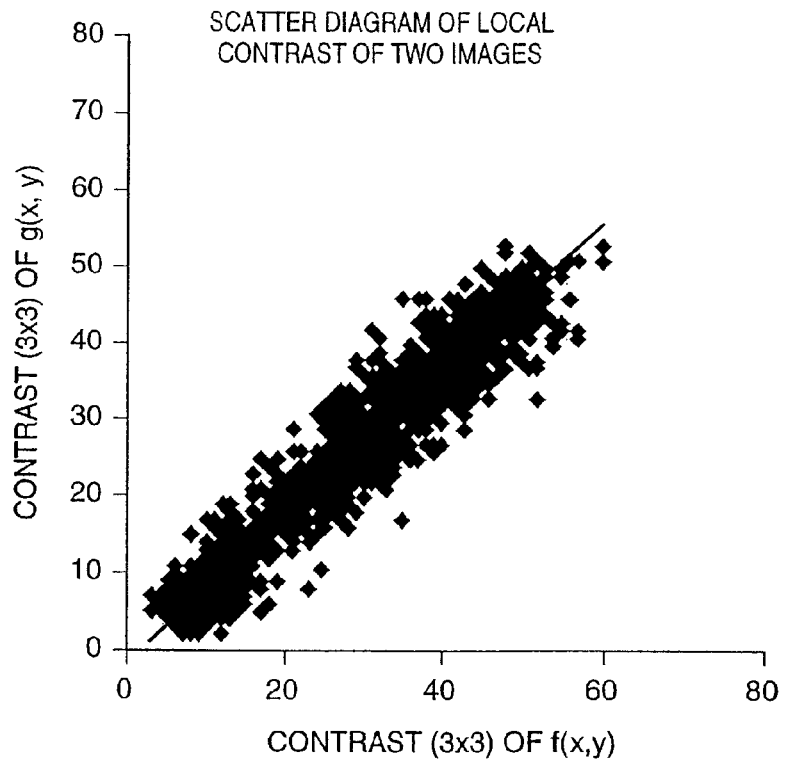
VALUE OF $V_e$

FIG. 23
3) AFTER ALIGNMENT OF SUB-PIXEL
| GRADIENT | INTERCEPT |
|---|---|
| 0.981 | −1.454 |
Vr= 168.393
Ve= 8.869
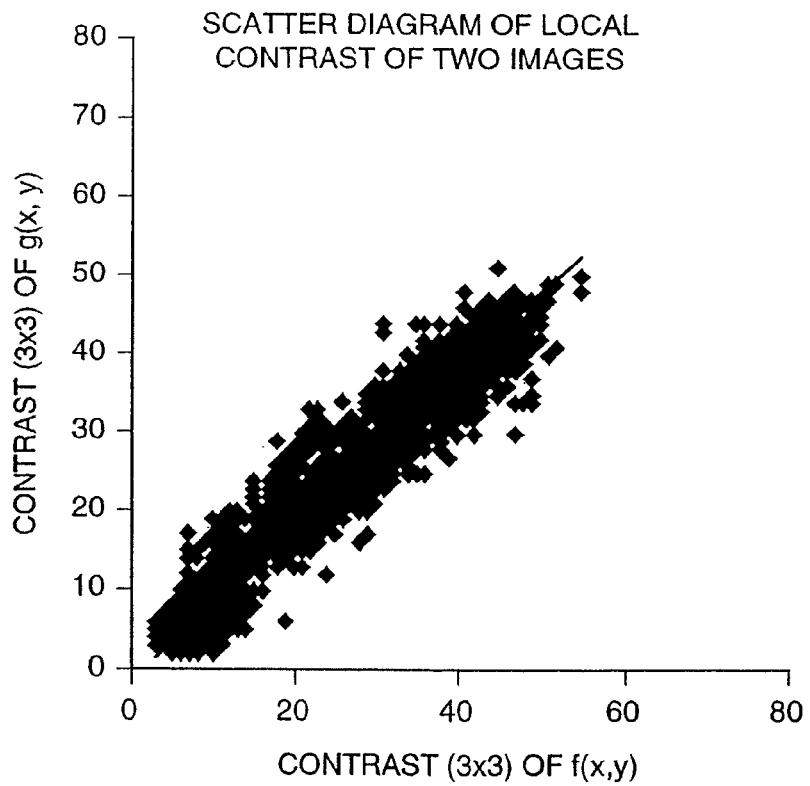
VALUE OF Ve
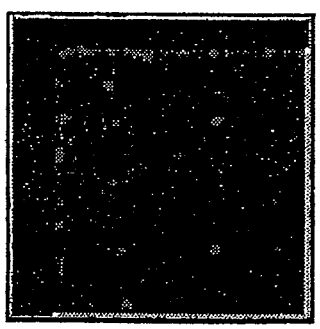

FIG. 30
SCATTER OF BRIGHTNESS OF TWO IMAGES
AND AMOUNT OF STATICS Ve
1) AFTER ALIGNMENT OF PIXEL UNIT
| GRADIENT | INTERCEPT |
|---|---|
| 0.705 | 55.947 |
Vr= 447.4806
Ve= 40.02821
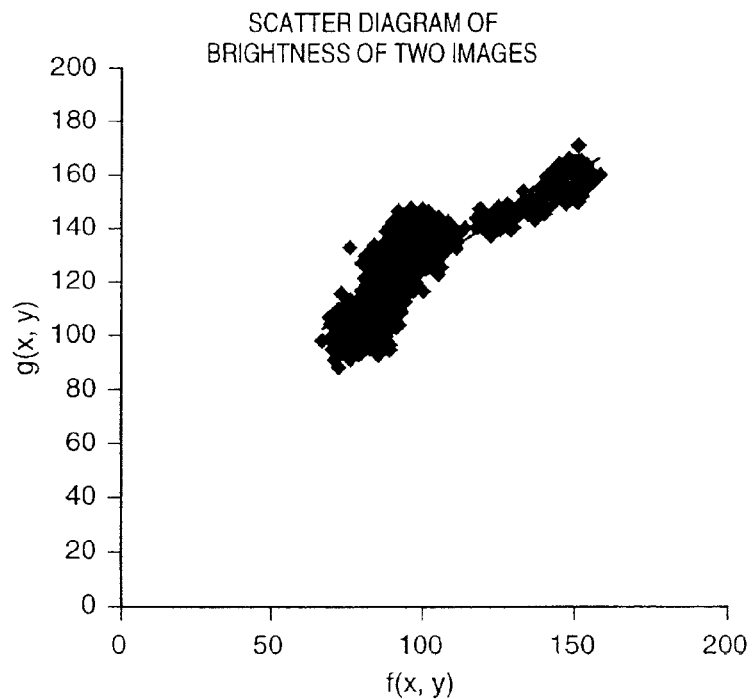
VALUE OF Ve
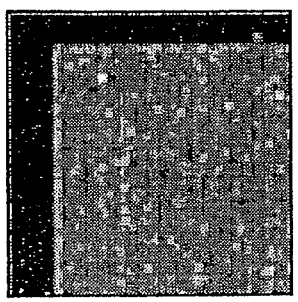

FIG. 31
2) AFTER BRIGHTNESS MATCHING
| GRADIENT | INTERCEPT |
|---|---|
| 0.986 | 2.567 |
Vr= 478.921
Ve= 8.598012
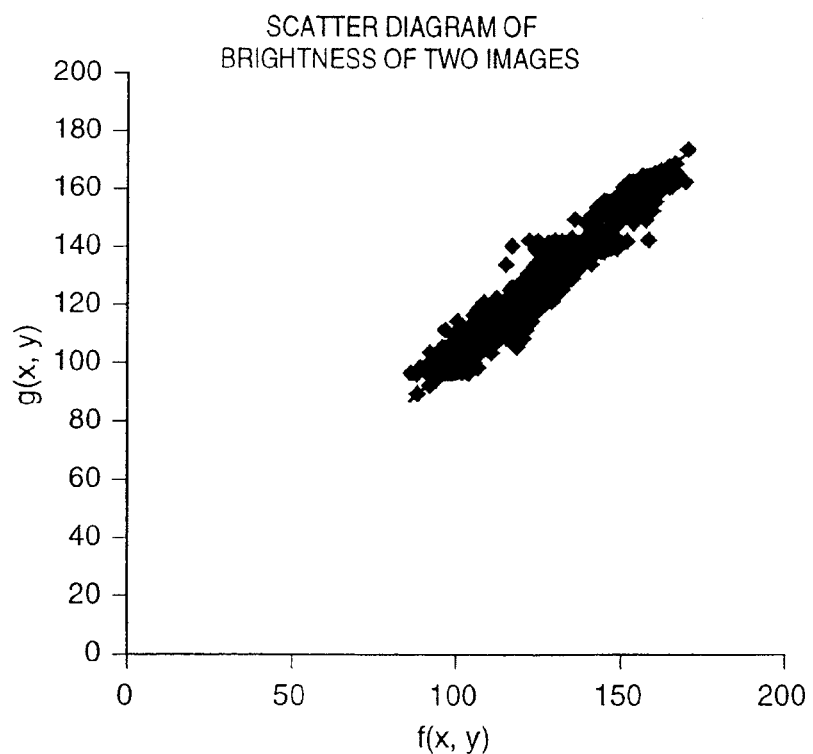
VALUE OF Ve
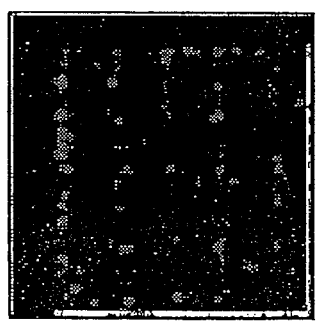

FIG. 32
3) AFTER FILTERING
| GRADIENT | INTERCEPT |
|---|---|
| 0.991 | 1.568 |
Vr= 473.2729
Ve= 7.477604
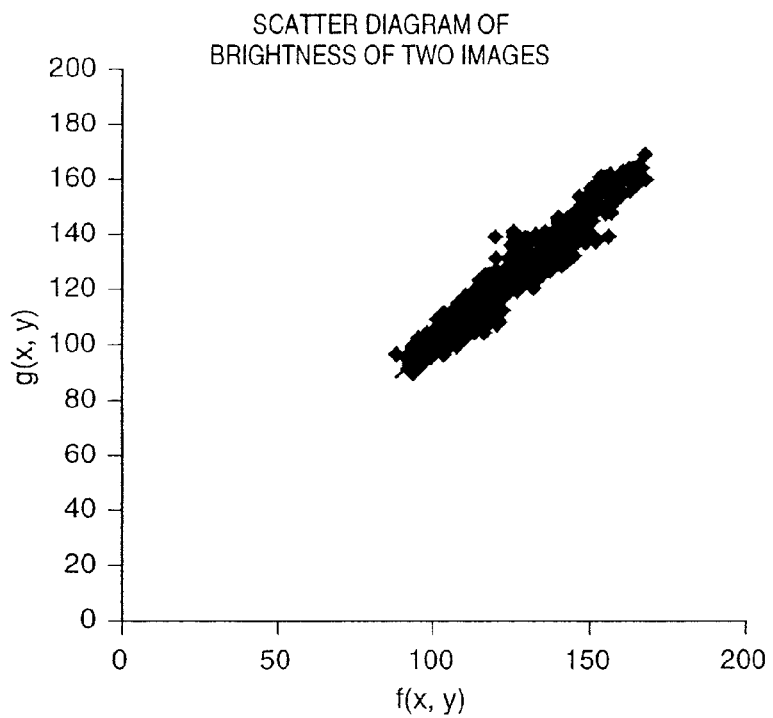
VALUE OF Ve
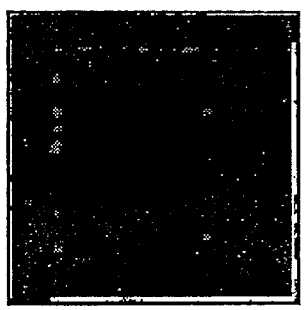

FIG. 39
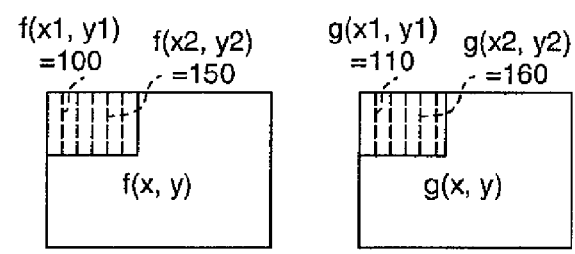
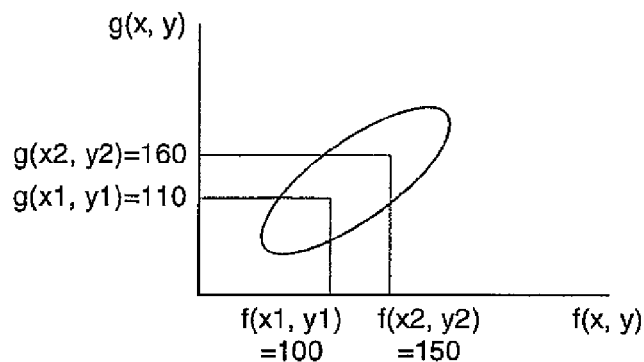
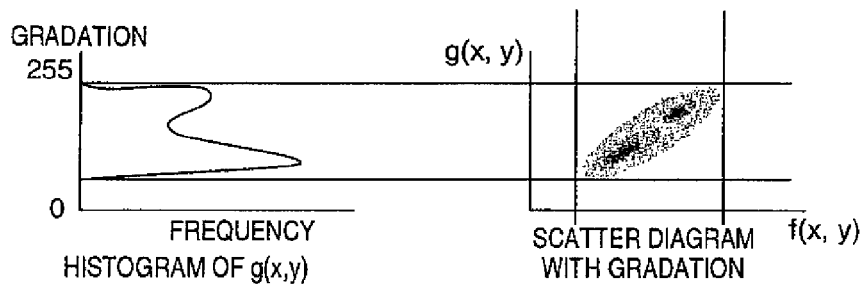
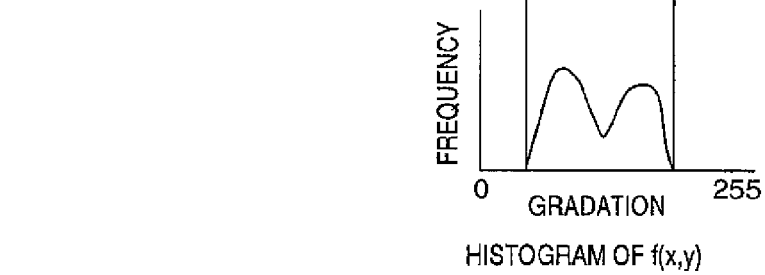
HISTOGRAM OF f(x,y)
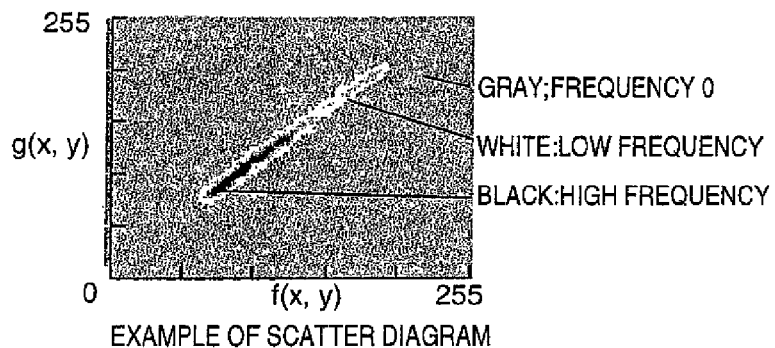
EXAMPLE OF SCATTER DIAGRAM FIG. 43A  1) AFTER ALIGNMENT WITH ACCURACY OF PIXEL UNIT
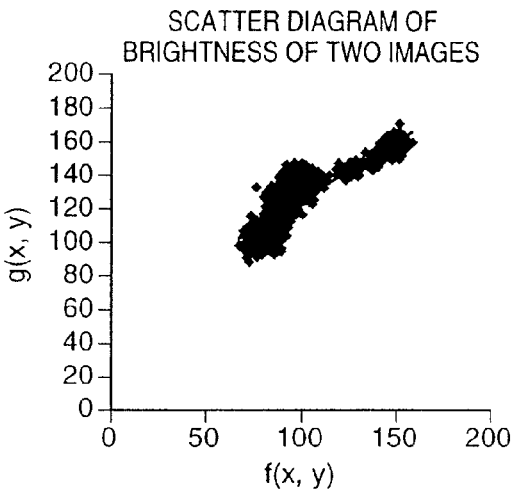
FIG. 43B  2) AFTER BRIGHTNESS MATCHING
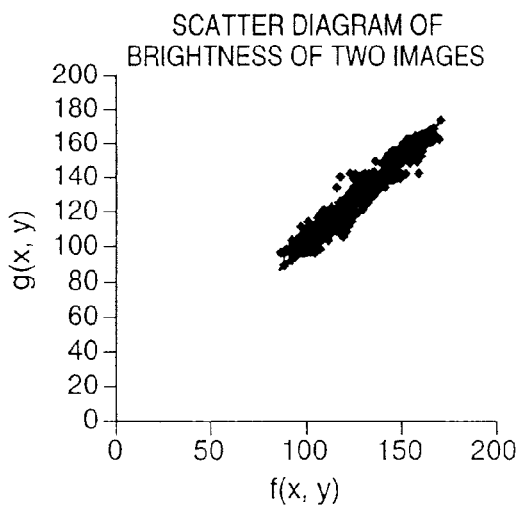

FIG. 44A

| DEFECT NUMBER | DEFECT COORDINATES | DEFECT AREA | DEFECT LENGTH | DEFECT BRIGHTNESS DIFFERENCE | DEFECT RELIABILITY (FREQUENCY INFORMATION) |
|---|---|---|---|---|---|
| 1 | (100.10, 202.20) | 4.54 | (2.2, 1.6) | 14 | 100 |
| 2 | (120.75, 232.72) | 10.2 | (2.9, 4.2) | 20 | 250 |
| 3 | | | | | |

FIG. 44B

| DEFECT NUMBER | DEFECT COORDINATES | DEFECT AREA | DEFECT LENGTH | DEFECT BRIGHTNESS DIFFERENCE | DEFECT RELIABILITY (DISTANCE INFORMATION) |
|---|---|---|---|---|---|
| 1 | (100.10, 202.20) | 4.54 | (2.2, 1.5) | 14 | 25 |
| 2 | (120.75, 232.72) | 10.2 | (2.9, 4.2) | 20 | 12 |
| 3 | | | | | |

FIG. 44C

| DEFECT NUMBER | DEFECT COORDINATES | DEFECT AREA | DEFECT LENGTH | DEFECT BRIGHTNESS DIFFERENCE | DEFECT RELIABILITY (POSITION INFORMATION) |
|---|---|---|---|---|---|
| 1 | (100.10, 202.20) | 4.54 | (2.2, 1.5) | 14 | (100, 200) |
| 2 | (120.75, 232.72) | 10.2 | (2.9, 4.2) | 20 | (250, 200) |
| 3 | | | | | |

DEFECT INSPECTION METHOD AND APPARATUS

CROSS-REFERENCE TO RELATED APPLICATIONS

This application is a continuation application of application Ser. No. 11/858,215, filed Sep. 20, 2007, now U.S. Pat. No. 7,512,259 which is a continuation application of application Ser. No. 11/204,181, filed Aug. 16, 2005 (now U.S. Pat. No. 7,274,813), which is a continuation application of application Ser. No. 09/294,137, filed Apr. 20, 1999 (now U.S. Pat. No. 6,947,587), based on Japanese Patent Application No. 10-110383, filed in Japan on Apr. 21, 1998 and No. 10-264275, filed Sep. 18, 1998, the contents of all of which are incorporated herein by reference in their entirety.

BACKGROUND OF THE INVENTION

The present invention relates to exterior inspection for detecting defects of patterns being examined, and particularly to a defect inspection method and apparatus for inspecting patterns in a semiconductor wafer or liquid crystal display.

In a conventional inspection apparatus of this kind, as disclosed in JP-A-55-74409, an image sensor such as a line sensor is used to detect the image of a pattern being examined while the pattern is being moved, and the detected image signal is compared in its gradation with another image signal delayed by a predetermined time, so that the inconsistency in the comparison can be recognized as a defect.

In addition, in another example disclosed in JP-2B-8-10463, two images are arranged in a row and compared with each other.

The above conventional defect recognition methods will be described in detail with reference to FIGS. 1, 2, 3 and 4. FIG. 1 is a schematic diagram of memory mats and peripheral circuits in a memory chip of the pattern being inspected in the prior art. FIG. 2 is a histogram of the brightness of the memory mats and peripheral circuits of the memory chip shown in FIG. 1.

FIG. 3 is a schematic diagram of a pattern being examined which pattern is processed to be flat by CMP (chemical mechanical).

A semiconductor wafer has formed thereon a large number of memory chips 20 one of which is illustrated in FIG. 1. The memory chip 20 can be divided roughly into memory mats 21 and peripheral circuits 22. Each of the memory mats 21 is a group of small repetitive patterns (cells), and the peripheral circuits 22 are fundamentally a group of random patterns. In most cases, if each memory mat is observed in detail, it can be recognized as a group of a plurality of patters repeated at different cell pitches.

FIG. 2 illustrates the distribution of the brightness of the memory mats 21 and peripheral circuits 22 in FIG. 1, or the frequency (histogram) with respect to the brightness of a memory chip expressed by ten bits, or in 1024 gradations, maximum. The memory mats 21 have a high pattern density and are generally dark. The peripheral circuits 22 have a low pattern density and are generally bright.

In the flattening process such as CMP shown in FIG. 3, the circuit pattern within the memory mat 21 changes the brightness with the pattern thickness as will be understood from the histogram of FIG. 4. This figure shows that the wiring layers are deposited and then flattened by CMP. In this pattern, the film thickness locally changes, easily causing irregular brightness. In the case of such a pattern, the brightness values on the pattern shown in FIGS. 2 and 3 are compared. If a threshold is set not to erroneously detect the brightness difference, the sensitivity to defect detection is extremely reduced. This brightness difference can be cancelled out to some extent if a wide wavelength band is used for illumination. However, because the pattern after CMP has sometimes a great change in brightness, there is a limit. Therefore, it has been desired to devise means for detecting minute defects from a pattern having irregular brightness.

Also, in a conventional example, the sum of the squares of the differences between corresponding parts of two pictures is calculated and applied to a paraboloid so that a positional shift between the pictures can be detected. This method, however, does not assure that the two images to be compared are coincident. Thus, optimum matching has been desired for the comparison. FIG. 5 shows experimental results of calculating the sum of the squares of the differences of opposite pixels of two pictures (f(x, y) in FIG. 13 in the later description) of which one picture is shifted by ±1 pixel in the x and y directions. The abscissa indicates the x direction, and the ordinate the y direction. Each value illustrated in the figure is the sum of the squares of the differences. Here, the same pictures (f(x, y) in FIG. 13) are used. That is, $\Sigma(f(x, y)-f(x\pm 1, y\pm 1))2$ is calculated as the sum of the squares of the differences. From FIG. 5 it will be seen that the sums of the squares of the differences even between the same pictures are not symmetrical with respect to the center (0, 0), or have an asymmetry of about 0.6%. Since the same pictures one of which is shifted are used, the sum of the squares of the differences is 0 at the point (0, 0). Therefore, even if the position where the sum of the squares of the differences is the minimum is calculated with a resolution of pixel size or below by applying a paraboloid to this data, a correct positional shift, or (0, 0) here cannot be detected.

Also, brightness is changed on the wafer after the flattening process such as CMP. The effect of this brightness change is illustrated in FIG. 6. Here, two pictures are used one of which has 1.1 times the brightness of the other. The brightness 1.1 times higher corresponds to the usual brightness change on the CMP wafer or below. Each value in the experimental results of FIG. 6 is the sum of the absolute values of the differences. The position where the minimum value is located is (0, 1). Thus there is a great error in terms of pixel level contrary to the resolution of pixel or below. The sum of the squares of the differences has the same tendency. From these data, it will be understood that the positional shift between pictures cannot be found precisely. Of course, for the brightness 1.05 times higher there is the same tendency. Thus, applying a paraboloid to the sum of the squares of the differences and calculating the position where the minimum value is obtained must be said to be means having very large error.

SUMMARY OF THE INVENTION

Accordingly, it is an object of the invention to provide a pattern defect inspection method and apparatus with the above problems solved, and capable of examining by comparing patterns of different brightness so that defects can be inspected with high sensitivity and high reliability at all times.

In addition, it is another object of the invention to provide a pattern defect inspection method and apparatus using a high-precision picture matching process.

Moreover, it is still another object of the invention to provide a pattern defect inspection method and apparatus capable of detecting with high sensitivity even for a wafer pattern after CMP.

In order to achieve the above objects, according to the invention, there is provided a method of inspecting defects of a plurality of patterns formed to be naturally the same on a substrate, wherein a first pattern being inspected is detected as a first image which is then stored, a second pattern being inspected is detected as a second image, and the second image is matched in brightness to the first image stored, and then compared with the first image so that the patterns can be inspected.

Moreover, according to the invention, there is provided a method of inspecting defects of a plurality of patterns formed to have naturally the same shape and flattened in their surfaces, wherein a first pattern being inspected is optically picked up as a first image signal and stored, a second pattern being inspected is optically picked up as a second image signal, at least one of the first image signal stored and the second image signal is locally changed in gradation, and the first and second image signals are compared so that the patterns can be inspected.

In addition, according to the invention, there is provided a method of inspecting defects of a plurality of patterns formed to be naturally the same on a substrate, wherein a first pattern being inspected is detected as a first image and stored, a second pattern being inspected is detected as a second image, the first image stored and the second image are corrected for their positional shift with an accuracy of pixel unit, the brightness of one or both of the corrected first and second images is changed, the first and second images changed in brightness as above are compared so that the inconsistency between the first and second images is detected as a defect, and the detected result is displayed.

Thus, according to the invention, the certainty of inconsistent information can be judged by using a scatter diagram of two detected images to be compared. In addition, since defects are detected by using information from the scatter diagram, the inspection can be made highly reliable. Moreover, use of the scatter diagram makes it possible to decide an appropriate threshold. Also, by using the certainty of inconsistent information, it is possible to effectively make defect review.

Therefore, reliable inspection data can be used by adding reliability. Furthermore, defects can be detected with high sensitivity without reducing the total inspection sensitivity by the brightness difference due to the change of the film thickness of a multilayer pattern. Therefore, in the manufacturing process of semiconductor devices, defects of patterns of a wafer after CMP can be detected with high precision and high reliability.

BRIEF DESCRIPTION OF THE DRAWINGS

FIG. 5 is a diagram showing the sum of the squares of the differences between two pictures.

FIG. 6 is a diagram showing the sum of the absolute values of the differences between two pictures.

FIGS. 13A-13C show examples of detected images and difference image according to the invention.

FIGS. 21-23 are scatter diagrams of local contrast at each image processing step on two pictures being compared.

FIGS. 30-32 are scatter diagrams at each image processing step on two images being compared.

FIG. 39 is a diagram showing the scatter diagram production and display according to the embodiment of the invention.

FIGS. 43A and 43B are scatter diagrams.

FIGS. 44A-44C show examples of output lists for defects.

DESCRIPTION OF THE EMBODIMENTS

Some embodiments of the invention will be described with reference to the accompanying drawings.

Embodiment 1

Figure 1:
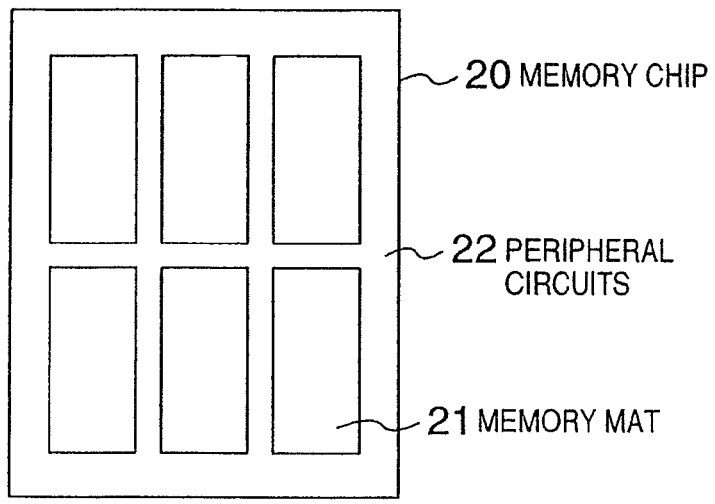
FIG. 1 is a schematic of the memory mats and peripheral circuits in a memory chip of which the pattern is to be inspected.
Figure 2:
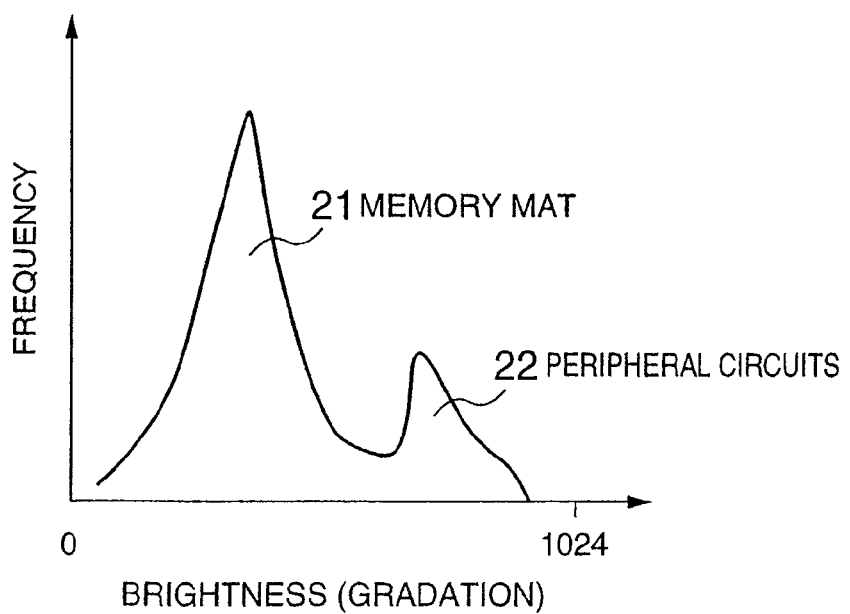
FIG. 2 is a histogram of brightness in the memory mats and peripheral circuits of the memory chip.
Figure 3:
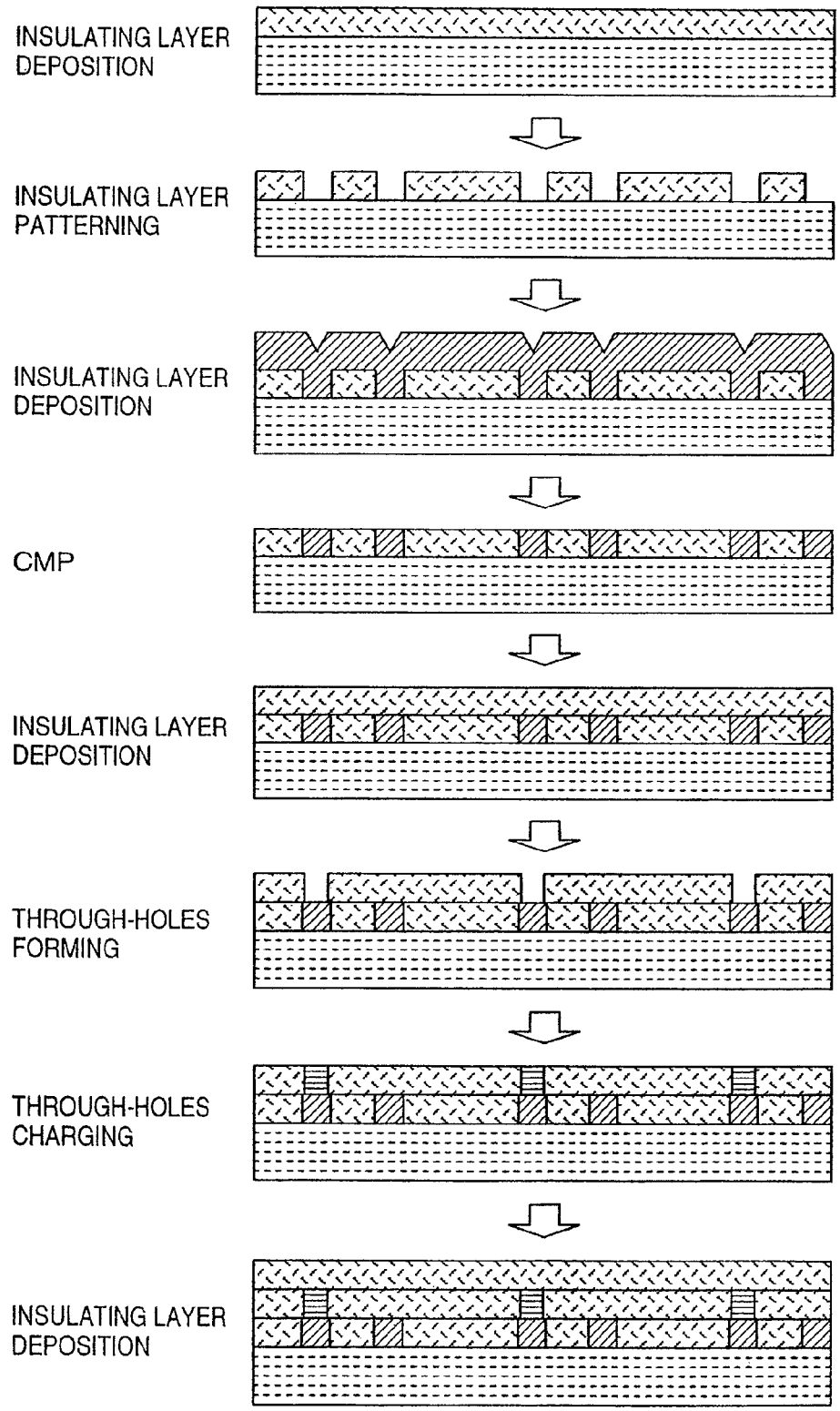
FIG. 3 is a diagram to which reference is made in explaining the flow of CMP.
Figure 4:
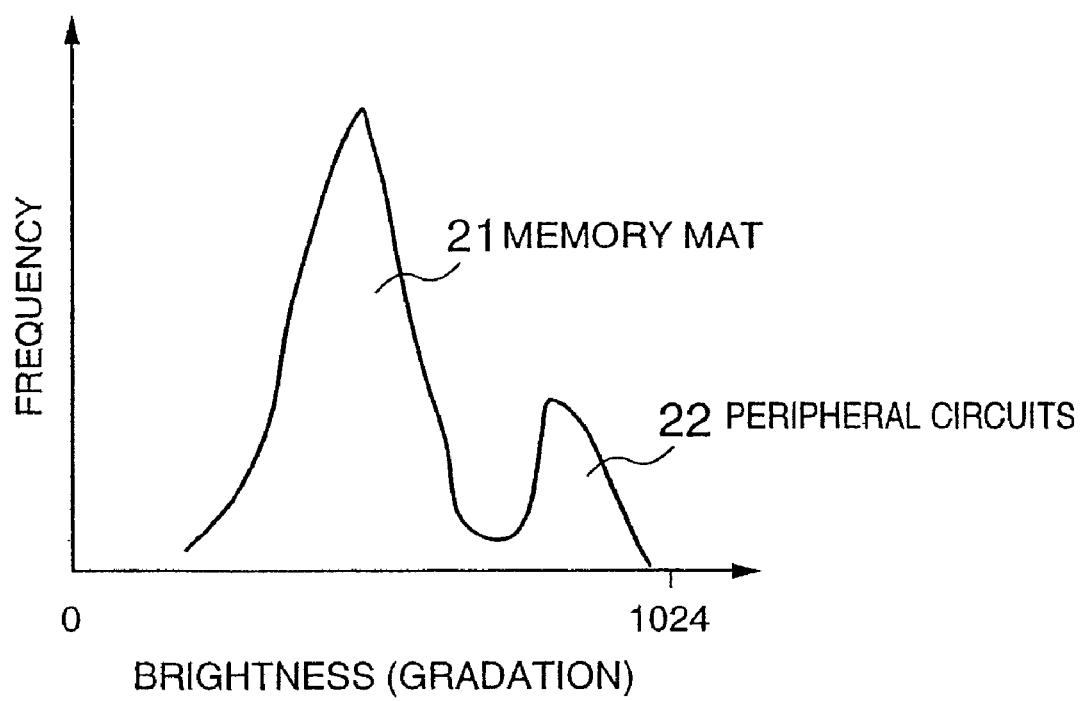
FIG. 4 is a histogram of brightness in the memory mats and peripheral circuits of a different memory chip after CMP.
Figure 7:
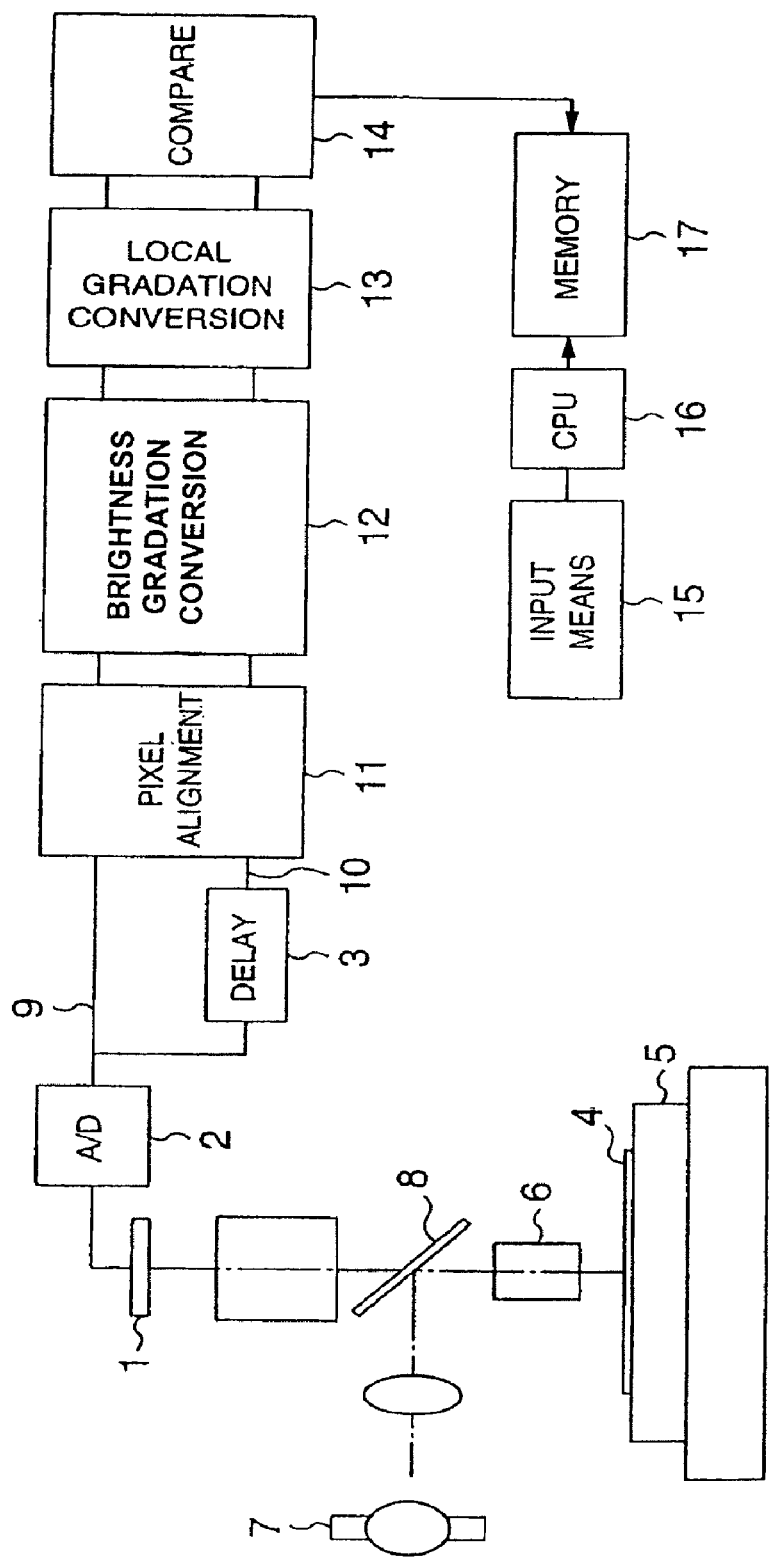
FIGS. 7 and 8 are block diagrams of pattern defect inspection apparatus according to one embodiment of the invention.
Figure 8:
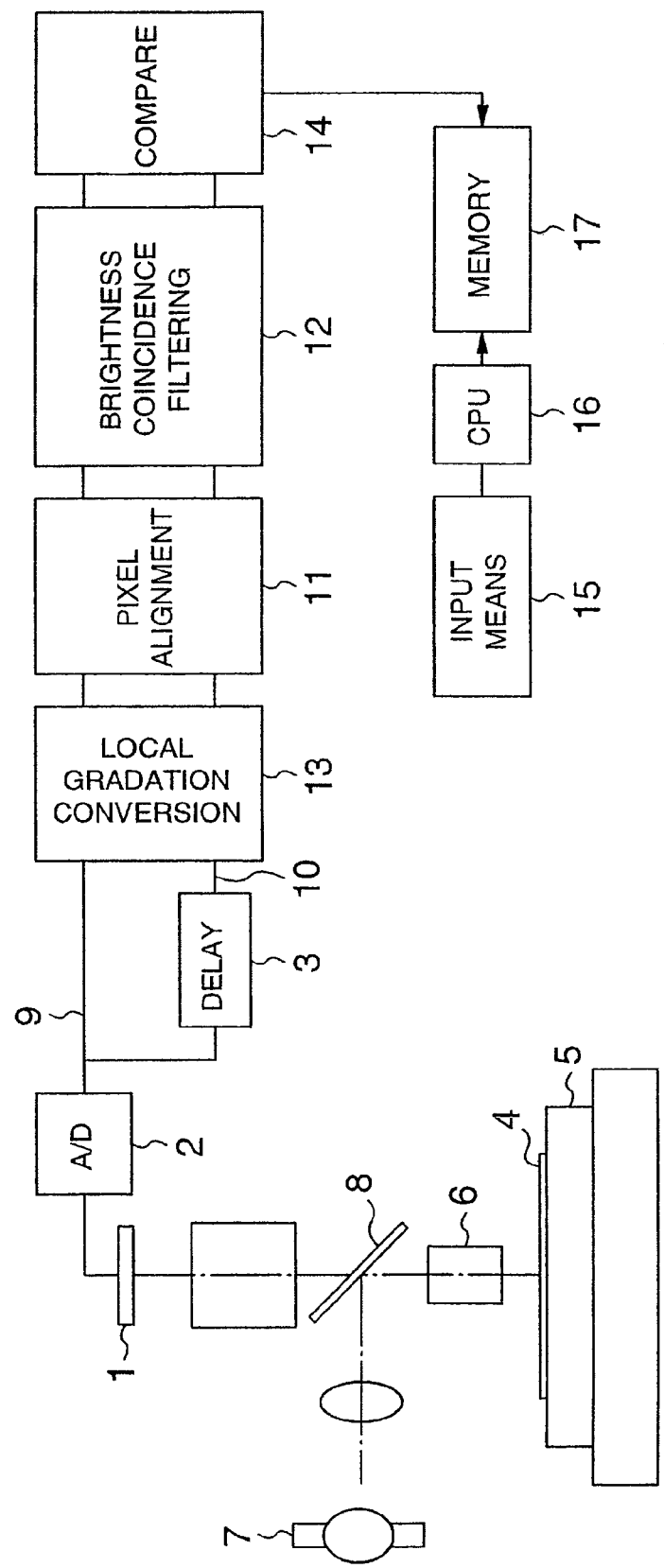

FIGS. 7 and 8 are block diagrams of pattern defect inspection apparatus according to the first embodiment of the invention.

It is assumed that this embodiment inspects, for example, patterns of a semiconductor wafer.

Referring to FIGS. 7 and 8, there are shown an image sensor 1 that responds to the brightness or gradation of light reflected from a semiconductor wafer 4 of patterns being inspected to produce a gradation image signal, an A/D converter 2 for converting the gradation image signal from the image sensor 1 into a digital image signal 9, a delay memory 3 for delaying the gradation image signal, and the semiconductor wafer 4 having patterns being inspected. There are also shown a stage 5 that is moved in X-direction, Y-direction, Z-direction and θ-direction (rotation) with the semi-conductor wafer 4 placed thereon, an object lens 6 facing the semiconductor wafer 4, a light source 7 for illuminating the semiconductor wafer 4 of the patterns being inspected, a half mirror 8 for reflecting the illumination light and supplying it through the object lens 6 to the semiconductor wafer 4 and at the same time allowing the reflected light from the semiconductor wafer 4 to permeate therethrough, and the digital image signal 9 into which the gradation image signal is converted by the A/D converter 2. Thus the light from the light source 7 for illumination is reflected to provide, for example, bright field illumination on the semiconductor wafer 4 through the object lens 6.

The delay memory 3 may be a delay memory for storing and delaying image signal 9 of a one-cell pitch or plurality-of-cells pitch repeated or may be another delay memory for storing and delaying image signal 9 of a one-chip pitch or plurality-of-chips repeated.

In addition, a block 11 is used to align the digital image signal 9 and a delayed digital image signal 10, or here to detect the amount of shift at which the minimum gradation difference can be obtained with a precision of pixel unit, and shift one picture on the basis of this amount of shift so as to align the two pictures. Here, the images are continuously detected by the image sensor, but divided at, for example, each 256 lines (the number of lines is determined according to the method described later), and the images of this unit are aligned. A block 12 is a brightness converter for converting both image signals that are different in brightness so that the brightness of one image signal equals to that of the other. Here, all the images are passed through a filter at a time so that the brightness of one image coincides with that of the other.

A block 13 is a gradation converter for converting the gradations of both image signals that are different in brightness so that the brightness of one image can be coincident with that of the other. Here, linear conversion is performed for each pixel by gain and offset so that the brightness coincidence can be achieved. The image signals from the gradation converter 13 are compared by a comparator 14, and the inconsistency can be detected as a defect.

The detected image signal is serially processed by a pipeline-type image processing system, and finally a defect and its features are produced.

Although bright field illumination is employed in the above example, the light source is not limited thereto, but may be an arbitrary one if it can be used as microscope illumination such as dark field illumination or ring band illumination. The illumination by an electron beam can be of course used.

The inspection may be performed a plurality of times with these illumination conditions changed so that the logical sum of the results from the plurality of inspection operations can be employed as the final result. Alternatively, it is possible that the logical product thereof is employed to assure the defect and that process diagnosis may be made by, for example, the distribution of defects or number of defects. In this case, the review for visual observation of inconsistent portions is not necessary, and thus the operation can be simplified and facilitated.

The operation of the inspection apparatus constructed as above will be described with reference to FIGS. 7~12. The order of processes in FIG. 7 is different from that in FIG. 8.

Referring to FIGS. 7 and 8, the stage 5 is moved at a constant speed in the X-direction so that the illumination light focused by the object lens 6 scans the necessary region of the patterns of semiconductor wafer 4 being inspected, while the image sensor 1 detects the brightness information (gradation image signal) of the pattern formed on the semiconductor wafer 4, or of the memory mats 21 and peripheral circuits 22 within the chip 20.

After the completion of one-row movement, the stage 4 suddenly moves with high speed to the next row in the Y-direction and positions itself. In other words, uniform movement and fast movement are repeated for the inspection. Of course, step and repeat type inspection may be performed. Then, the A/D converter 2 converts the output (gradation image signal) from the image sensor 1 into the digital image signal. This digital image signal 9 has a format of 10 bits. Although the image processing can be well performed without particular problem even if the signal has about 6 bits, a certain number of bits larger than that is necessary for the detection of minute defects.

First the pixel-unit alignment between images will be mentioned. In this alignment, one of two pictures to be compared is shifted pixel by pixel from the other while the gradation difference (the difference between each pixel of one picture and the corresponding pixel of the other) is calculated, and the amount of shift at which the gradation difference is the minimum is found. The range of shift between pictures to be detected is set, for example, within ±3 pixels, maximum but changed according to the design rule of pattern. Thus, the two pictures are aligned by shifting one picture by the obtained amount of shift.

A method for the alignment will be described below.

$$S(\Delta x, \Delta y) = \Sigma |f(x,y) - g(x - \Delta x, y - \Delta y)| \qquad (1)$$

The shift detection is performed by detecting $\Delta x$, $\Delta y$ when the above $S(\Delta x, \Delta y)$ becomes the minimum.

However, since the position satisfying the minimum is obtained only when the picture is shifted pixel by pixel, this position is added with an offset depending on whether the true position is near to $\Delta x$ or $\Delta y$.

According to the expressions given below, $\Delta x$ and/or $\Delta y$ are added with 1 or nothing, that is, if $S(1,0)+S(1,-1)+S(0,-1)$ is the minimum, then $\Delta x$++ (2)

if $S(-1,0)+S(-1,-1)+S(0,-1)$ is the minimum, then nothing (3)

if $S(-1,0)+S(-1,-1)+S(0,1)$ is the minimum, then $\Delta y$++ (4)

and if $S(-1,0)+S(1,1)+S(0,1)$ is the minimum, $\Delta x$++, $\Delta y$++ (5)

where $\Delta x$++ means $\Delta x = \Delta x + 1$.

Thus, two pictures can be always aligned by shifting one picture by the obtained amount of shift. In other words, a picture f is always shifted to the upper right to be a new picture f'. The movement direction can be limited to one of four directions (lower right, upper left, lower left and upper right). This leads to the simplification of hardware.

Figures 9, 10:
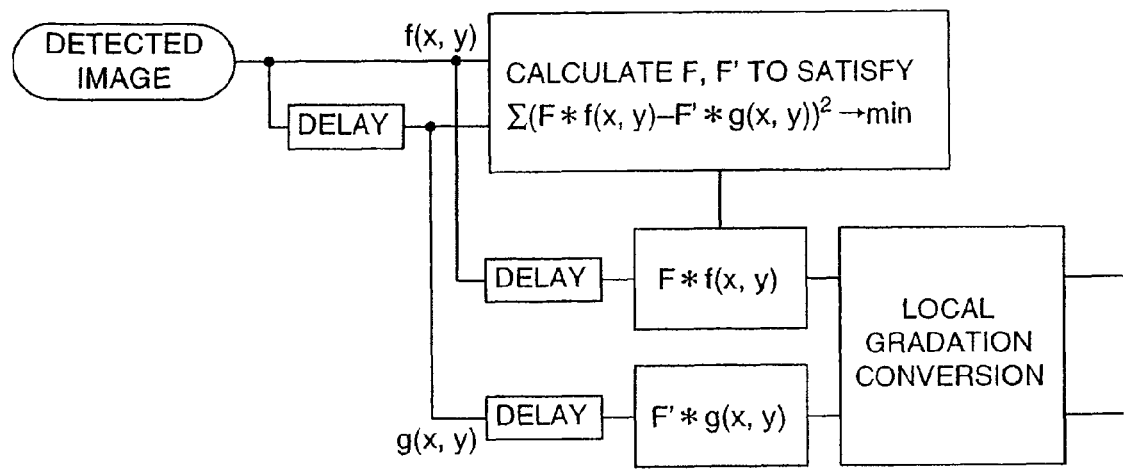
FIG. 9 is a detailed block diagram of an image brightness coincidence filter operation unit 12 in FIGS. 7 and 8.
FIG. 10 shows an example of a twin filter.

FIG. 9 is a detailed block diagram of the brightness coincidence filter operation unit 12. First, filters F, F' are found that make the following expression the minimum within two pictures f(x, y), g(x, y) that are aligned with accuracy of pixel unit.

$$\Sigma(F*f(x,y) - F'*g(x,y))^2 \qquad (6)$$

The filters F, F' have a size of for example 2×2 pixels.

FIG. 10 shows examples of filters. The filters F and F' are symmetrical, and a twin as illustrated. If the filters are of the twin type, the coefficients of the filter parameters can be solved by using the method of least squares.

$$\alpha = \frac{|(\Sigma\Sigma C0 * Cy)*(\Sigma\Sigma Cx * Cy) - (\Sigma\Sigma C0 * Cx)*(\Sigma\Sigma Cy * Cy)|}{|(\Sigma\Sigma Cx * Cx)*(\Sigma\Sigma Cy * Cy) - (\Sigma\Sigma Cx * Cy)*(\Sigma\Sigma Cx * Cy)|} \quad (7)$$

$$\beta = \frac{|(\Sigma\Sigma C0 * Cx)*(\Sigma\Sigma Cx * Cy) - (\Sigma\Sigma C0 * Cy)*(\Sigma\Sigma Cx * Cx)|}{|(\Sigma\Sigma Cx * Cx)*(\Sigma\Sigma Cy * Cy) - (\Sigma\Sigma Cx * Cy)*(\Sigma\Sigma Cx * Cy)|} \quad (8)$$

where $$C0 = f(x,y) - g(x,y) \quad (9)$$

$$Cx = |f(x+1,y) - f(x,y)| - |g(x-1,y) - g(x,y)| \quad (10)$$

$$Cy = |f(x,y+1) - f(x,y)| - |g(x,y-1) - g(x,y)| \quad (11)$$

This system filters the two pictures and makes the square error of the gradation the minimum to reach coincidence. No repetitive computations are necessary, or a single calculation is made to achieve the object.

The feature of this system is that the filter coefficients α, βD are found so that the gradations of two pictures can be well coincident in terms of square error minimum. Particularly, these parameters do not necessarily indicate the true amount of shift of picture. For example, as described about the prior art it can be considered to apply a paraboloid to S(Δx, Δy), calculate the minimum gradation difference position, and then find interpolating pixels by interpolation on the basis of this calculated position. In this case, there is no rule or conditions to be met for the brightness, and thus it is not guaranteed to use the obtained pictures for the comparative inspection. In addition, under a different brightness, it is not clear what the computed shift shows. In addition, even if the minimum gradation difference position calculated approximately to a paraboloid is coincident with that obtained according to the system used in this embodiment, the produced pictures to be compared are not coincident.

Figure 11:
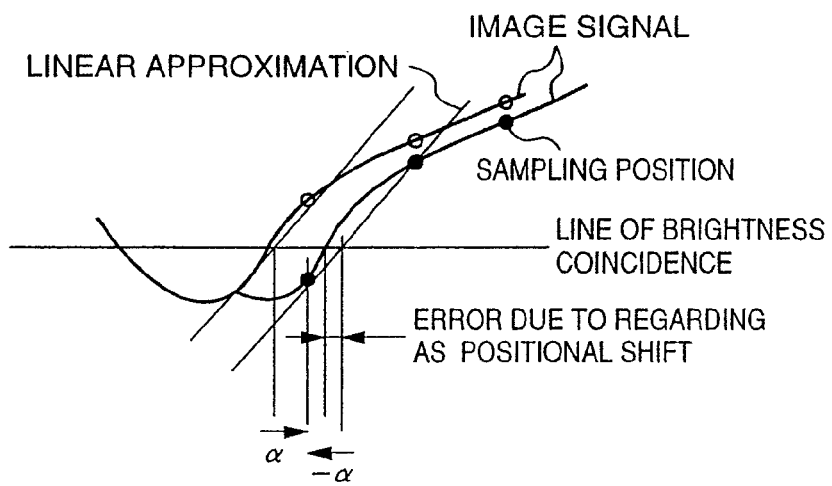
FIG. 11 is a diagram to which reference is made in explaining the operation of the image brightness coincidence filter operation unit 12.

The proposed matching system assures that the difference between the squares of the brightness values of two pictures becomes the minimum. Thus, in this point this system is different from the other systems. As illustrated in FIG. 11, because of linear approximation, the coefficient α of filter has error for a positional shift. However, the obtained brightness values are coincident. This system can substantially reduce the gradation difference between images, and thus it is much appropriate for the comparative and inspection.

Moreover, the filter coefficients α, β can be calculated analytically without repetitive computation, and thus this system is suitable to be formed as certain hardware.

Figure 12:
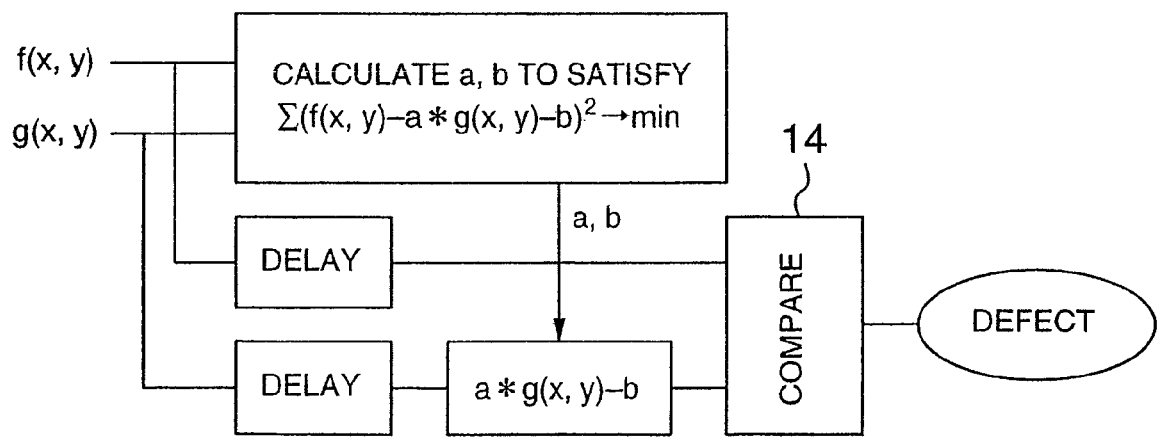
FIG. 12 is a detailed block diagram of a local gradation converter 13.

FIG. 12 is a detailed block diagram of the local gradation converter 13. The two pictures f(x, y), g(x, y) that are aligned with accuracy of pixel unit and produced from the brightness coincidence filter operation unit are processed so that parameters a, b (a: gain, b: offset) can be produced which make the following expression the minimum within a certain area of the pictures.

$$\Sigma(f(x,y) - a*g(x,y) - b)^2 \quad (12)$$

The parameters a, b can be calculated by partially differentiating the above expression with respect to a, b and making the resulting expression equal to zero. For example, the certain area is a range of 7 around each point.

The g(x, y) as one of the image signals is converted by use of the obtained parameters into $$a*g(x,y) + b \quad (13)$$

Thus, pictures coincident in bright can be obtained. The parameters a, b can take different values for each position (x, y).

$$a = (\Sigma(f(x,y)g(x,y)) \cdot \Sigma f(x,y)\Sigma g(x,y)/MN)/(\Sigma g(x,y)g(x,y) - \Sigma g(x,y)\Sigma g(x,y)/MN) \quad (14)$$

$$b = (\Sigma f(x,y) - a\Sigma g(x,y))/MN \quad (15)$$

where MN is the number of pixels in the range of Σ.

In addition, within the rang of Σ, the brightness of the aimed center pixel is compared with that of the surrounding pixels. If the brightness values of those pixels are greatly different, it will be better not to add those values.

Alternatively, the addition itself is made, but it will be effective to weight the values before the addition, thereby lowering percent contribution. For example, if the brightness of the aimed pixel at (x, y) is represented by c, and that of another pixel within the range of Σ by d, then the weight (x, y) can be expressed by $$W(x,y) = \max[1 - (c-d)^2/(D*D), 0] \quad (16)$$

where max[ ] is the maximum value detection, the brightness c, d is of 8 bits gradation, and D is a constant.

Thus, if the brightness of the aimed center pixel is similar to that of the surrounding pixels, the weight is selected to be substantially equal to 1. If it is not similar, the weight is smaller than 1. Although D is a constant, it may be changed according to the brightness, or D=func (c). Moreover, decision is made of whether or not the pixel belongs to the same pattern. If the average brightness of different patterns is represented by μ, D may be given by D=|c−μ|. If there are three or more different patterns, D may be selected to be the difference between similar patterns. Of course, it is not necessary to stick to this form. Other means may be used if weights are properly provided.

FIGS. 13A and 13B show examples of two detected images. The two detected images f(x, y), g(x, y) have different brightness as illustrated. The two images were aligned with precision of pixel unit, and subjected to the brightness coincidence filter operation. However, since these images have an excessively large difference in brightness, a great inconsistency is caused in the difference image as illustrated in FIG. 13C. This image was subjected to the gradation conversion process.

FIGS. 14A~16B show examples of the process. That is, FIGS. 14A~16A and 14B~16B illustrate two detected images g(x, y), f(x, y), converted image a*g(x, y)+b, and their brightness histograms, respectively. Here, D was selected to be 70, or D=70.

Figure 14A:
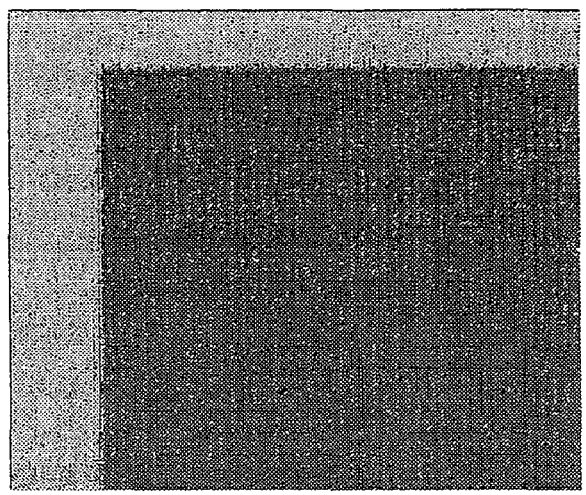
FIGS. 14A-14B, 15A-15B, 16A-16B, 17A-17B and 18A-18B show examples of the gradation conversion according to the invention.
Figure 14B:
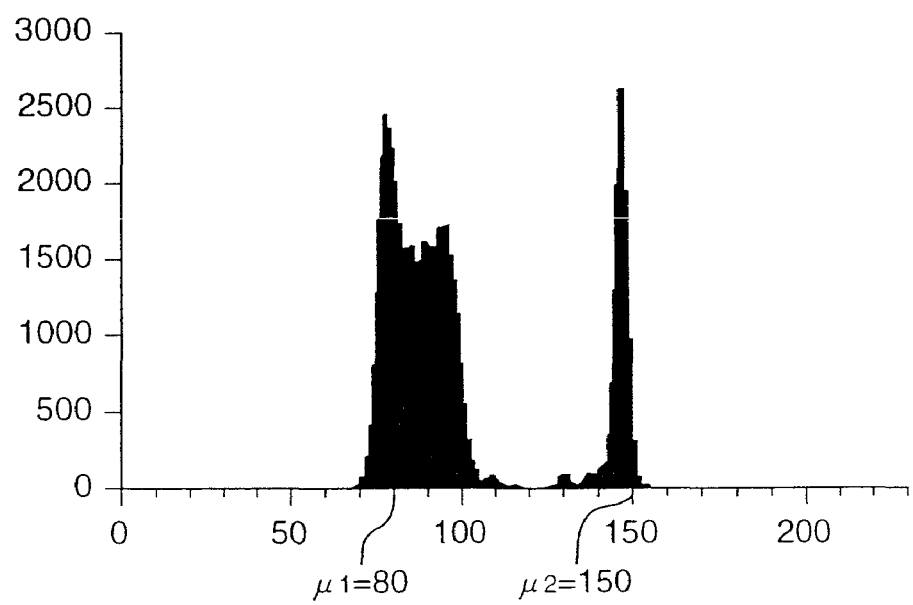
Figure 15A:
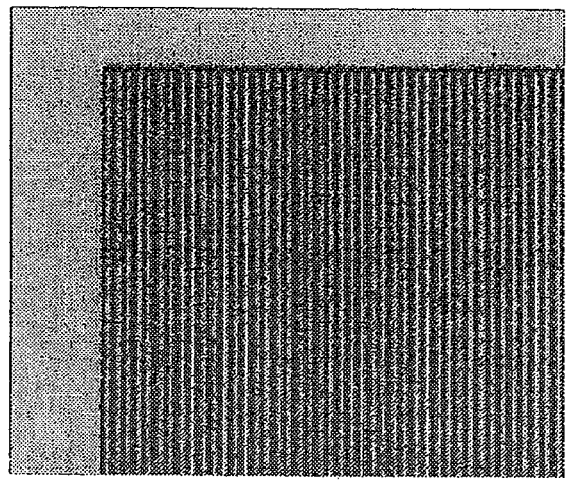
Figure 15B:
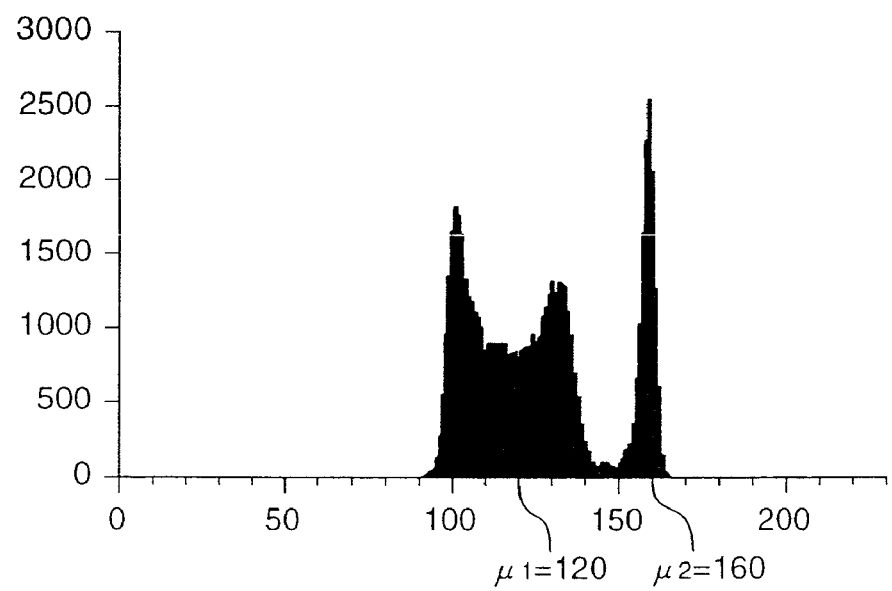
Figure 16A:
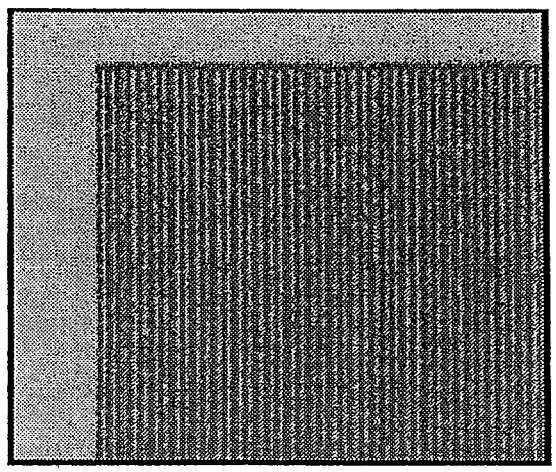
Figure 16B:
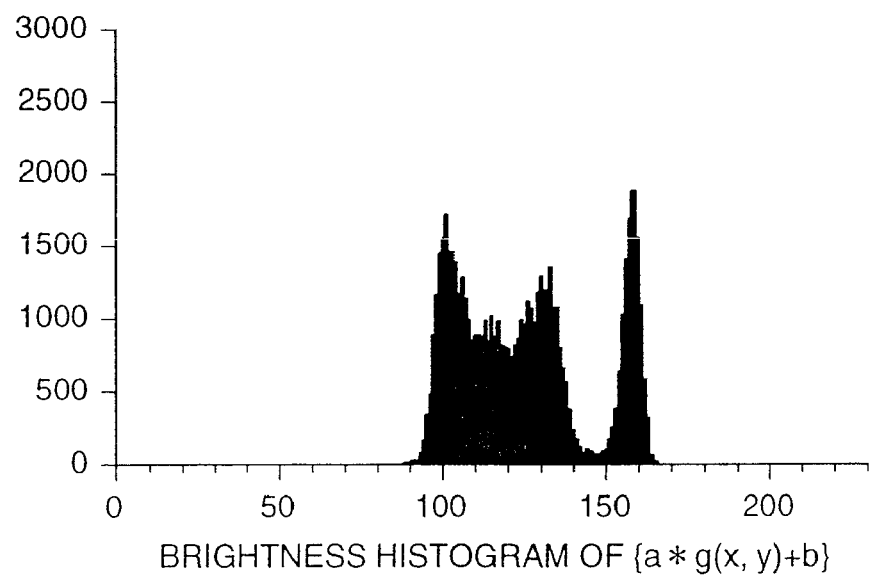
Figure 17A:
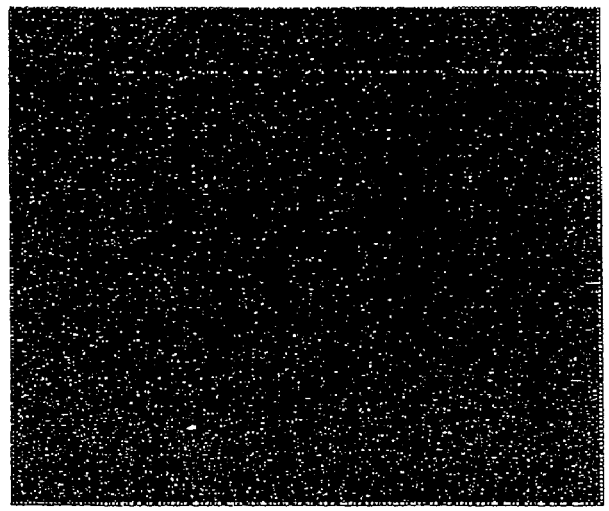
Figure 17B:
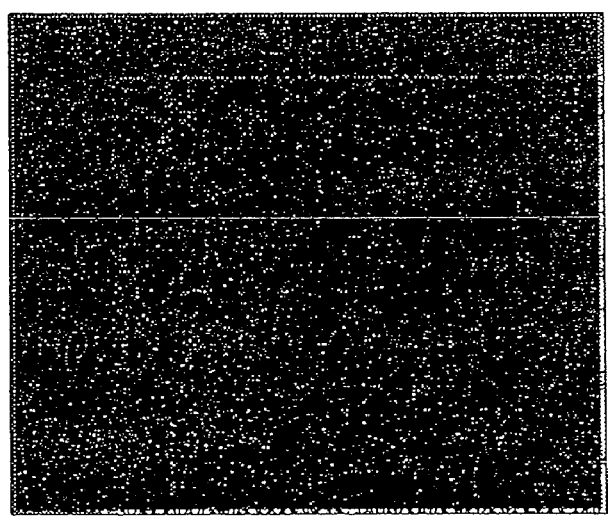
Figure 18A:
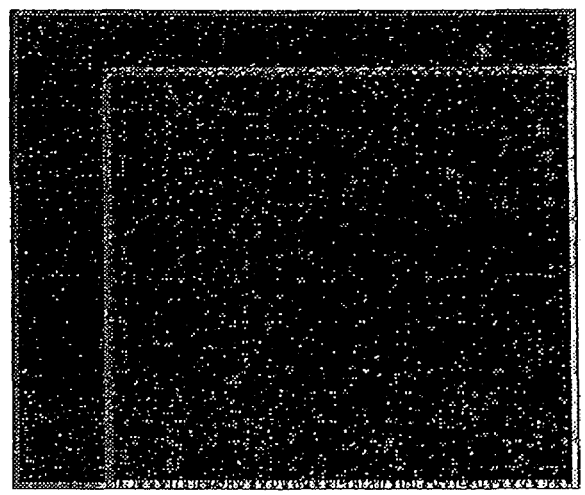
Figure 18B:
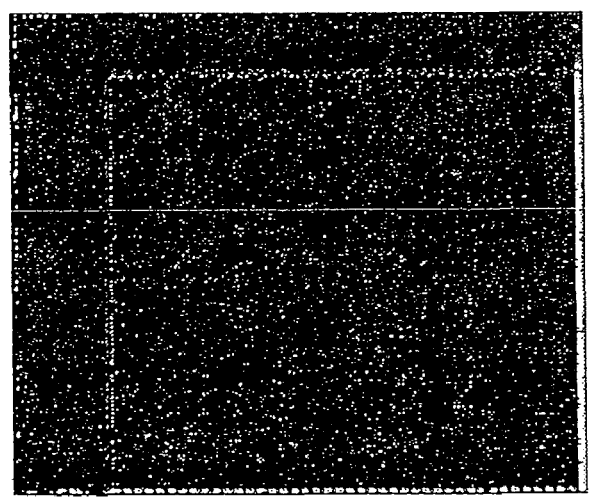

As will be understood from the histogram shown in FIG. 14B, the value D corresponds to the difference between the average brightness values of the two distributions of the double hump response histogram. In other words, the weight W with this D serves as an index for indicating whether or not the brightness belongs to the same distribution. The decided area is the range of 7×7 pixels around each point. From FIGS. 14A~16B, it will be seen that the brightness histograms are made substantially equal by the conversion. Here, after the experiment on the images shown in FIGS. 14A~16A, the parameters a, b of a=1.41, b=0 were obtained at certain points within the images. In addition, it will be understood that the brightness gains in the images are greatly different (41%).

From the above example, it can be considered that the offset b is always fixed to 0, and that the gain is made variable.

The offset and gain may be determined according to the characteristics of patterns to be considered and apparatus structure.

FIGS. 17A, 17B and 18A, 18B show the differences between the images obtained by the conversion. In the first three images of FIGS. 17A, 17B and 18A, 18B, the decided areas are the ranges 3×3, 5×5, 7×7 around each point. At this time, the weight is equal to 1, or W(x, y)=1. In addition, in the last image, the decided area is the range 7×7, and the weight depends on the above-mentioned W(x, y). From these figures, it will be seen that when the area is small, the brightness values are locally added and that the inconsistency between images becomes small. The allowance of brightness is extended, but minute defects will be missed. Therefore, it is necessary to spread the area according to the defects being detected. However, if the weight is fixed to 1, the boundary between the patterns will be detected as inconsistency, or false report. If weighting is made, the effect of the boundary is reduced, two images are substantially equal in brightness, and a minute defect can be detected.

The area such as 7×7 pixels is not necessarily square, but may be a rectangle, polygon or circle. The area is not limited to such very small regions, but may be a region as large as (hundreds of pixels)×(hundreds of pixels). In short, the area may be within a range in which the brightness variation can be absorbed.

The weight can also be selected to be 0 when the brightness difference between the aimed center pixel and the peripheral pixels is larger than a threshold.

In addition, the following gradation conversion can be considered.

$$W(x,y)(\sigma_f/\sigma_g)(g(x,y)-m_g)+m_f \quad (17)$$

where $\sigma_f$, $\sigma_g$ and $m_f$, $m_g$ are the standard deviation and average value within a certain area near a point (x, y) in the image f(x, y), g(x, y), respectively.

By the above conversion, it is possible to make the brightness of the image g(x, y) coincident with that of the image f(x, y).

The weight W(x, y) may be the above values or correlation coefficients of image data within a certain area in the images f(x, y) and g(x, y).

This system has a feature that the histograms of two images eventually coincide with each other.

Either system takes a linear conversion form of gain and offset.

The above-mentioned gradation conversion is the local brightness conversion in the vicinity of the aimed pixel. Of course, the gradation conversion may be applied to the whole image, or here to all the 256 lines according to the object and image characteristics. In addition, when the brightness of one of two images is made coincident with that of the other, the brightness of a brighter image can be decided to use as a reference by calculating, for example, the average brightness values of each two images, and comparing them, or by calculating the average brightness values of each certain areas or points.

Although the gradation conversion is executed after the image brightness coincidence filter operation as in FIG. 7, this order may be reversed as in FIG. 8.

The comparator 14 may be the means shown in the system developed by the inventors and disclosed in JP-A-61-212708. This comparator is formed of a difference image detector, an inconsistency detector for converting the difference image into a binary signal on the basis of a threshold, and a feature extraction circuit for calculating an area, a length (projection length), coordinates and so on from the binary output.

Figure 19:
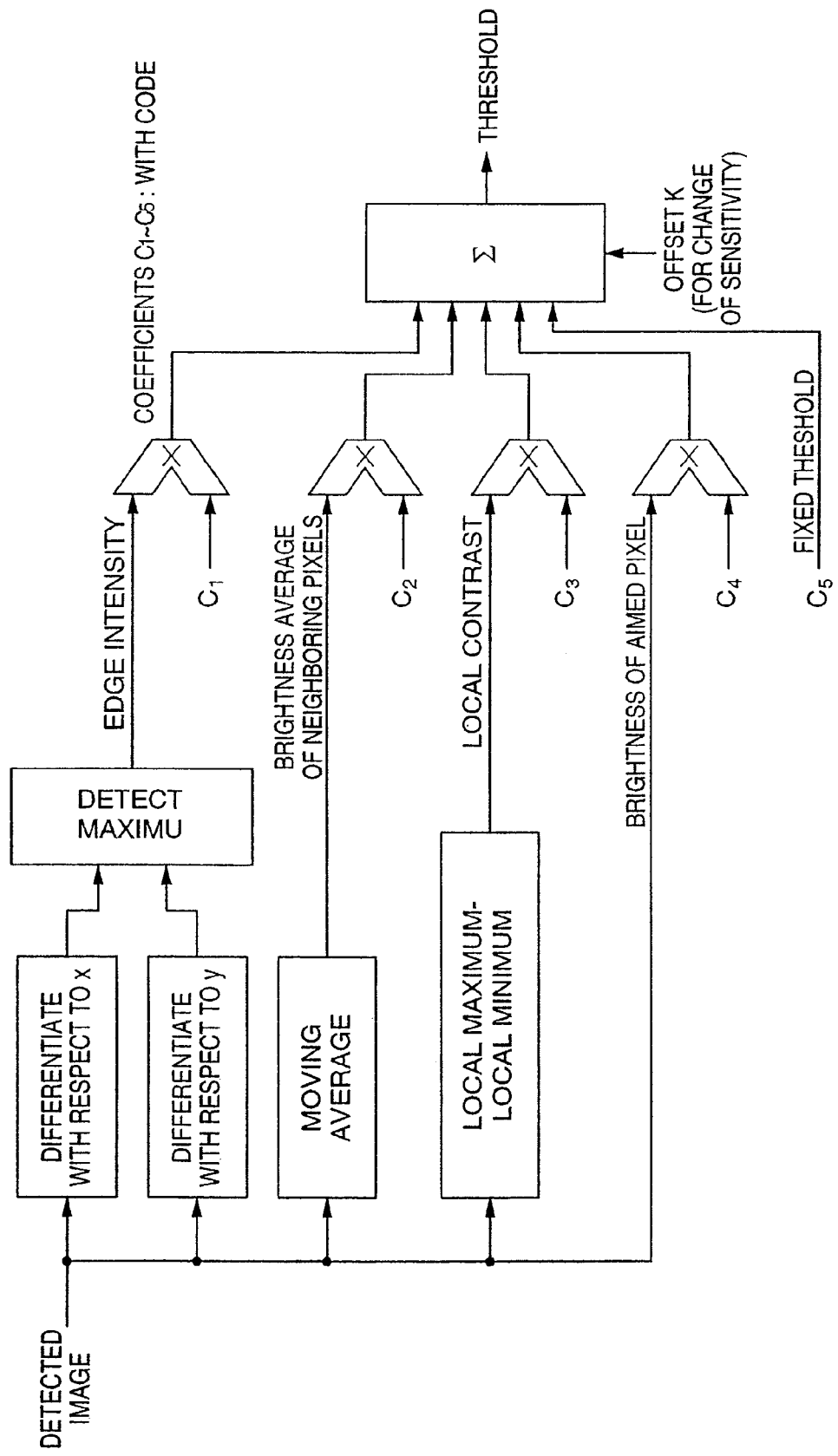
FIGS. 19 and 20 are diagrams to which reference is made in explaining threshold setting systems.

The selection of a threshold for use in the conversion to binary values according to the invention will be further described with reference to FIGS. 19 and 20.

When a difference image is converted into a binary signal, false report is easy to occur at the boundary between regions as described above. Thus, as illustrated in FIG. 19, the detected image is processed at each point to produce by computation a difference between the maximum and the minimum, an average value and a larger one of the differentiated values of x, y (hereinafter, referred to as local data) within a local region. These produced values are multiplied by separately determined parameters, and added, or subjected to the so-called multiplication addition calculation, thereby generating a threshold. Accordingly, since the differentiated values increase at, for example, the boundary between regions where the brightness change is large, the threshold increases, thus preventing the false report from being caused. Of course, it is not necessary to provide all the three values of the difference between the maximum and the minimum, the average value and the large one of the differentiated values of x, y, but only one may be produced. For example, if the gradation conversion is performed, the average value is not necessary to compute.

If the difference between images is converted into a binary signal by using the threshold, the false report problem can be effectively reduced. The local data can be obtained more easily by finding distributions from the scatter diagram described later. FIGS. 21~23 show scatter diagrams of the difference between the maximum and the minimum within a local region of images. A line segment is drawn on this distribution data, and error from the line segment is found. This process is executed for each local data, and then a threshold can be determined by the multiplication and addition.

For example, it is assumed that the threshold Th is calculated from the following equation.

$$Th = C3 \times (\text{local contrast}) + C2 \times (\text{average brightness}).$$

where the local contrast image is defined by the maximum minus the minimum of 3×3 pixels, and the average brightness image is expressed by the moving average of 3×3 pixels.

The two local contrast images to be compared are represented by f(x, y), g(x, y), and Ve calculated from $$Ve = \frac{1}{(2dx+1)\cdot(2dx+1)-2} \sum_{x=-dx1}^{dx} \sum_{y=-dy}^{dy} \left( \frac{g(x,y)-}{(m \cdot f(x,y)+n)} \right)^2 \quad (18)$$

is made equal to σk.

Similarly, the brightness average images are represented by f(x, y), g(x, y), and the calculated Ve is made equal to σa.

Thus, the following equation (19) can be determined.

$$\sigma g = C3 \times \sigma k + C2 \times \sigma a \quad (19)$$

The same is done for another image. Thus, coefficients C2, C3 can be found.

In order to solve the above equation of Th, the standard deviation σk is determined which is the distance from a straight line of gradient 1 (m=1), interception 0 (n=0) to each plot data point in the local contrast scatter diagram and which corresponds to error. Similarly, the standard deviation σa is found which is the distance from a straight line of gradient 1, interception 0 to each plot data point in the scatter diagram of average brightness, and which corresponds to error. In addition, the standard deviation σg is estimated which is the distance from a straight line of gradient 1, interception 0 to each plot data point in the brightness scatter diagram of the two original images, and which corresponds to error.

These values are substituted into the above equation Th, giving rise to an equation having C2 and C3 like the equation (19). This operation is performed for images at different points, thus producing other equations of different coefficients C2 and C3. These equations are solved as simultaneous equations, so that coefficients C2, C3 are definitely determined. Thus, the threshold Th can be calculated from the above equation with known C2, C3. Of course, the threshold Th may be given by $$Th=C3\times(\text{local contrast})+C2\times(\text{average brightness})+\text{offset}.$$

For another setting system, the floating threshold to be estimated may be given by the following equation (20) that is a linear connection of local brightness contrast and average values. The parameters are calculated by multiple regression analysis with reference to the scatter diagram information of two pictures being compared.

$$Th=C0+C1\times|\overline{f-g}|+C2\times|\overline{f}|+C3\times|f'|+C4\times|\overline{f}| \qquad (20)$$

The procedure for the setting will be given below.
(1) Detect images at a plurality of points (a set of two chips).
(2) Generate a brightness scatter diagram from data of detected image and reference image (using images not including defects or images with defects removed).
(3) Find points enveloping a set of data in the scatter diagram (extract a point of frequency 1 in estimation), and extract local contrast and average data from the pixels of image corresponding to the points.
(4) Adjust the parameters C0~C4 by multiple regression analysis on the basis of the information obtained by the step (3).
(5) Select data to be used according to p value (significance level) (find a combination in which the p value is a much reliable value (0.05 or below)).
(6) Calculate threshold images from the estimated parameters C0~C4, and compare with difference images.
(7) Add false report if present, and adjust the parameters C0~C4.
(8) Make a test inspection.
(9) Repeat the steps (7) and (8) if a false report occurs.

Figure 20:
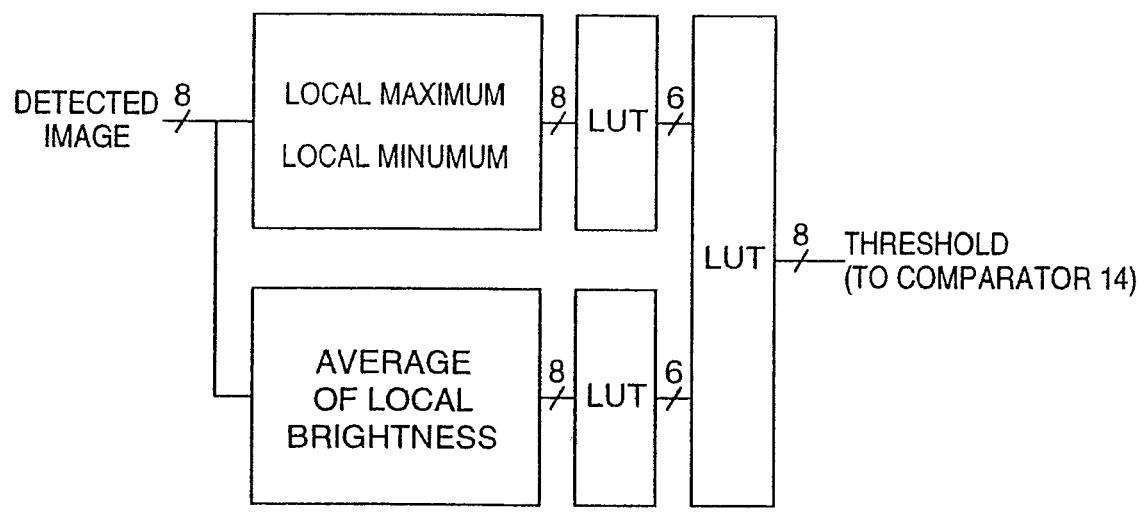

In addition, as shown in FIG. 20, look-up tables (LUTs) may be used in place of the multiplication addition operation of coefficients and error mentioned above. As illustrated in FIGS. 19 and 20, the detected image is processed to produce local maximum values and local minimum values, and the contrast of the difference therebetween, and then fed to the LUT. Similarly, the detected image is processed to produce a local average value, and fed to the LUT. The outputs from these LUTs are supplied to another LUT, thereby producing a threshold. The circuit arrangements shown in FIGS. 19 and 20 limit the number of bits being used to 8→6 in order for the scale of the LUTs to be appropriate. The estimated threshold is supplied to the comparator (FIGS. 7 and 8) 14, where it is used as a threshold for the conversion to a binary signal. The data of the contents of the LUTs are produced by using various images which are processed by the same procedure as above to produce error which is then interpolated.

The images to be selected are of course in the place where error is easy to detect. The prior art does not use this way of deciding. The feature of the present invention is not only the establishment of the procedure but also theoretical decision.

Referring to FIGS. 7 and 8, input means 15 formed of a keyboard, a disk or the like supplies to a CPU 16 coordinates of array data within the chips on the semiconductor wafer 4 which are obtained from the design information. The CPU 16 generates defect inspection data on the basis of the inputted coordinates, and supplies it to a memory 17.

This defect inspection data can be indicated on display means such as a display or supplied to the outside from the output means.

In addition, the operator can visually confirm that the gradation conversion is properly made for inspection by displaying the image before the gradation conversion or image data and image after the gradation conversion or image data or by displaying image after the gradation conversion or image data.

Thus, images can be compared with high precision, and the object of the invention can be achieved with high sensitivity.

While this embodiment employs bright field illumination, the images obtained by dark field illumination can be used for the inspection. Also, the kinds of defects can include defective shapes such as short-circuits or open-circuits or other foreign bodies.

Embodiment 2

Figure 24:
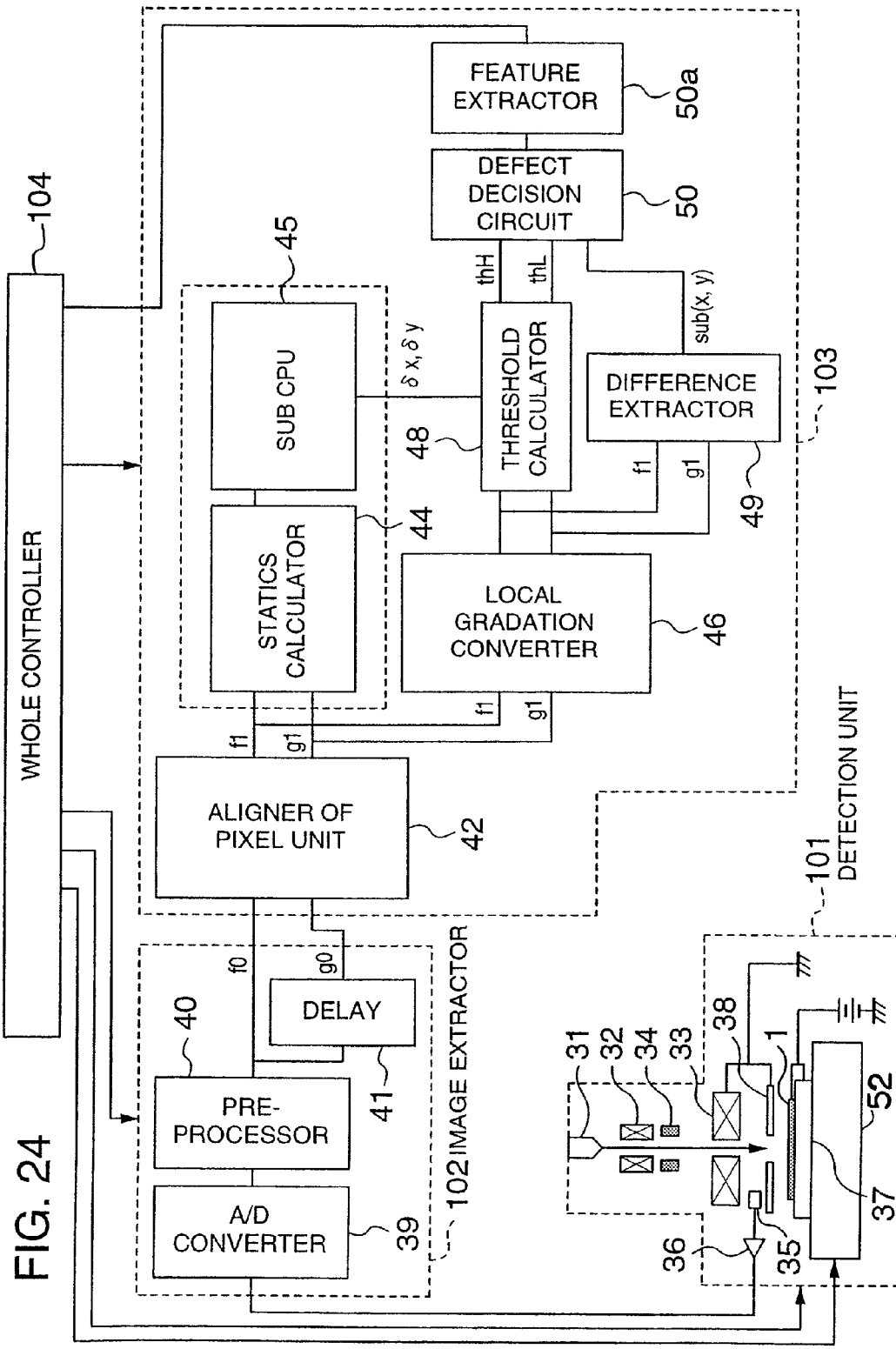
FIG. 24 is a block diagram of a pattern defect inspection apparatus according to another embodiment of the invention.

FIG. 24 shows the second embodiment of a pattern inspection method and apparatus according to the invention. In this embodiment, an electron beam is used to scan the sample and the electrons generated from the wafer by the irradiation of the electron beam are detected. An electron beam image of the scanned region is thus obtained on the basis of the change of the intensity, and used to make a pattern inspection. The second embodiment overcomes the problems to be solved by the invention by setting a defect decision threshold for each pixel considering pattern shift and different gradations.

This system includes a detection unit 101, an image extractor 102, an image processor 103, a whole controller 104 for controlling the whole system.

The detection unit 101 will be described first.

Referring to FIG. 24, an electron beam emitted from an electron gun 31 passes through a magnetic field lens 32 and an object lens 33 and focused on the sample surface to an extent of about pixel size in diameter. In this case, a negative potential is applied to the sample by a ground electrode 37 and a retarding electrode 38 to decelerate the electron beam between the object lens and the sample, thereby achieving high resolution in the low-acceleration voltage region. When the electron beam is irradiated on the sample, the sample (wafer 1) emits electrons. A deflector 34 deflects the electron beam so that the electron beam repeatedly scans the sample in the X-direction, and at the same time the sample is continuously moved in the Y-direction with the stage 2. The sample generates electrons in synchronism with the repetitive X-direction scanning and the continuous Y-direction movement, thus producing a two-dimensional electron beam image of the sample. The electrons emitted from the sample are caught by a detector 35, and the signal is amplified by an amplifier 36.

In this system, it is desired that a fast-deflection static deflector be used for the deflector 34 for permitting the electron beam to repeatedly scan in the X-direction, that a thermal field emission type electron gun that can emit a large electron beam current and thus reduce the irradiation time be used as the electron gun 31, and that a semiconductor detector capable of fast driving be used for the detector 35.

The image extractor 102 will be described next.

The amplified signal from the amplifier 36 is converted into a digital signal by an A/D converter 39, and fed to a pre-processor 40. The pre-processor makes the input signal be subjected to dark level correction (the dark level is the average of the gradations of particular pixels during the beam blanking period), electron-beam-current fluctuation correction (the beam current is detected by an object diaphragm not shown and the signal is normalized by the beam current), and shading correction (correction for the variation of light intensity due to beam scan position). Thereafter, in the pre-processor, the signal is subjected to filtering process by a Gaussian filter, an averaging filter or a edge emphasizing filter so that the picture quality can be improved. If necessary, image distortion is corrected. This pre-processing is made for the detected image to be converted favorably to the later defect decision processing.

A delay circuit 41 delays the signal by a constant time. If the delay time is made equal to the time in which the stage 52 is moved by one-chip pitch, the delayed signal g0 and the non-delayed signal f0 become the image signals at the same locations of the adjacent chips, and thus can be used for the previously mentioned chip comparative inspection. Alternatively, if the delay time is set to correspond to the time in which the stage 5 is moved by the pitch of memory cell, the delayed signal g0 and the non-delayed signal f0 become the image signals at the same locations of the adjacent memory cells, and thus can be used for the previously mentioned cell comparative inspection.

Thus, the image extractor 102 produces the image signals f0 and g0 being compared. Hereinafter, f0 is referred to as the detected image, and g0 as the compared image.

The image processor 103 will be described.

A pixel-unit aligner 42 shifts the compared image so that the location at which the "degree of matching" between the detected image as a reference and the compared image is the maximum lies within 0~1 pixel.

Then, the filters F, F' in the brightness coincidence filter operation unit are determined to make the brightness inconsistency between the images the minimum. As described above, it is necessary to estimate various different statistics $\Sigma\Sigma xx$ in order to solve the equations (7), (8) for the parameter coefficients dx0, dy0 of filters by the method of least squares. A statistics calculator 44 computes various statistics $\Sigma\Sigma xx$, and a sub-CPU 45 receives the statistics and calculates $\alpha$, $\beta$ from the equations (7), (8).

A local gradation converter 46 makes gradation conversion, permitting the above-mentioned f1 and g1 to coincide in brightness.

A difference extractor 49 estimates a difference image sub(x, y) between f1 and g1. That is, the following equation is satisfied.

$$\mathrm{sub}(x,y)=g1(x,y)-g1(x,y) \quad (21)$$

Figure 25:
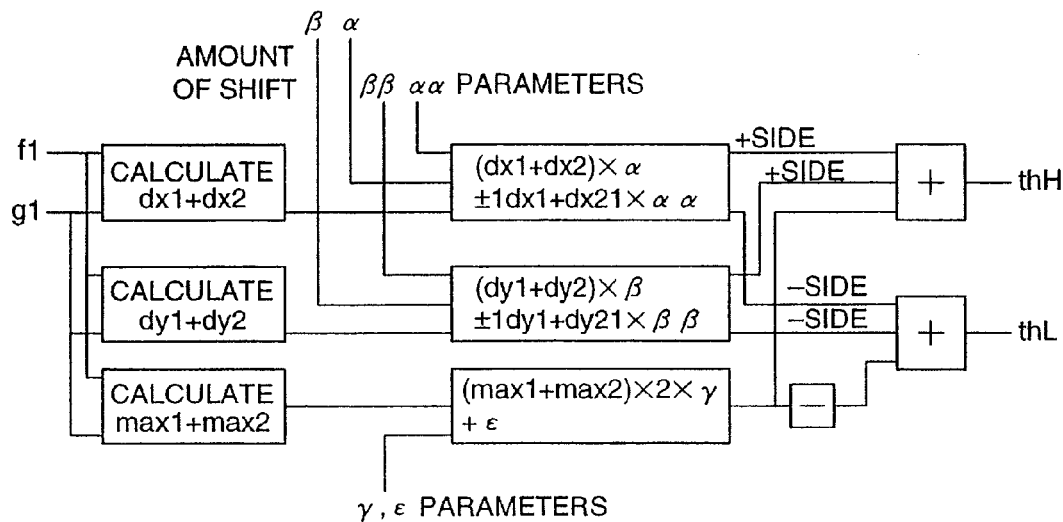
FIG. 25 is a block diagram of a threshold computation circuit 48.

A threshold calculator 48 receives the image signals f1, g1 produced from the local gradation converter 46 and $\alpha$, $\beta$, and computes two thresholds thH(x, y) and thL(x, y) by which decision is made if the difference image sub(x, y) has a defect. The threshold thH(x, y) regulates the upper limit of the sub(x, y), and the threshold thL(x, y) does the lower limit of the sub(x, y). FIG. 25 shows the arrangement of the threshold calculator 48. The equations for the calculation in the threshold calculator will be given below.

$$thH(x,y)=A(x,y)+B(x,y)+C(x,y) \quad (22)$$

$$thL(x,y)=A(x,y)-B(x,y)-C(x,y) \quad (23)$$

in which $$\begin{aligned}
A(x, y) &= |dx1(x, y)*\alpha - dx2(x, y)*(-\alpha)| + \\
&\quad |dy1(x, y)*\beta - dy2(x, y)*(-\beta)| \\
&= |dx1(x, y) + dx2(x, y)|*\alpha + \\
&\quad |dy1(x, y) + dx2(x, y)|*\beta
\end{aligned} \quad (24)$$

$$\begin{aligned}
B(x, y) &= \|dx1(x, y)*\alpha\alpha - dx2(x, y)*(-\alpha\alpha)\| + \\
&\quad \|dy1(x, y)*\beta\beta - dy2(x, y)*(-\beta\beta)\| \\
&= \||dx1(x, y) + dx2(x, y)|*\alpha\alpha| + \\
&\quad \||dy1(x, y) + dy2(x, y)|*\beta\beta|
\end{aligned} \quad (25)$$

$$C(x, y) = (\max1 + \max2)/2 * \gamma + \varepsilon \quad (26)$$

where aa, bb are real numbers of 0~0.5, $\gamma$ is a real number larger than 0, and $\epsilon$ is an integer larger than 0.

$$\begin{aligned}
dx1(x, y) &= f1(x+1, y) - f1(x, y) \\
dx2(x, y) &= g1(x, y) - g1(x-1, y) \\
dy1(x, y) &= f1(x, y+1) - f1(x, y) \\
dy2(x, y) &= g1(x, y) - g1(x, y-1) \\
\max1 &= \max\begin{vmatrix} f1(x, y), f1(x+1, y), \\ f1(x, y+1), f(x+1, y+1) \end{vmatrix} \\
\max2 &= \max\begin{vmatrix} g1(x, y), g1(x-1, y), \\ g1(x, y-1), g(x-1, y-1) \end{vmatrix}
\end{aligned} \quad (27)$$

The first term A(x, y) of the right side of equations (22), (23) for the calculation of thresholds is provided for correcting the threshold in accordance with $\alpha$, $\beta$ estimated by the shift detector 43. For example, dx1 (x, y) expressed by equation (27) is regarded as a local rate of change in the x-direction of the gradation of f1, and dx1 (x, y)($\alpha$ is a prediction value of change of the gradation of f1 shifted by $\alpha$. Thus, the first term, {dx1 (x, y)*$\alpha$−dx2 (x, y)*(−$\alpha$)} of A(x, y) is a prediction value of how the gradation of the difference image between f1 and g1 is changed for each pixel when the images f1 and g1 are shifted $\alpha$, and −$\alpha$ in the x-direction, respectively. Similarly, the second term is a prediction value in the y-direction. The first term A(x, y) of the threshold is provided for canceling $\alpha$, $\beta$.

The second term B(x, y) of the right side of equations (22), (23) for the calculation of thresholds is provided for allowing very small shift of pattern edge, minute difference of pattern shape and pattern distortion. When the equation (24) for A(x, y) and equation (25) for B(x, y) are compared, it will be understood that B(x, y) is the absolute value of the prediction of gradation change of the difference image with aa, bb. If the known shift (regarded) is cancelled by A(x, y), the addition of B(x, y) to A(x, y) means the shifting (regarded) of the aligned state by aa in the x-direction and by bb in the y-direction. That is, B(x, y) allows shifting aa in the x-direction and bb in the y-direction.

The subtraction of B(x, y) from A(x, y) means the shifting of the aligned state by −aa in the x-direction and −bb in the y-direction. −B(x, y) allows shifting −aa in the x-direction and −bb in the y-direction. Provision of upper and lower thresholds results in allowing the shift of ±aa, ±bb. The allowance of shift can be controlled freely by setting the parameters aa, bb at proper values.

The third term C(x, y) of equations (22), (23) for the calculation of thresholds is provided for allowing the very small difference between gradations. The addition of C(x, y) means allowing that the gradation of g1 is C(x, y) larger than that of f1. The subtraction of C(x, y) means allowing that the gradation of g1 is C(x, y) smaller than that of f1. Although C(x, y) in this embodiment is expressed by the sum of a typical gradation (here the maximum) in a local region, multiplied by a proportional constant γ and a constant ϵ, it is not necessary to be limited to this function, but may be a function suitable for a known way of gradation change, if present. If it is known that the variation width is proportional to the square root of gradation, C(x, y)=(max1+max2)½*y+ϵ should be used in place of the equation (26). As in B(x, y), the gradation difference allowance can be controlled freely by parameters γ, ϵ.

A defect decision circuit 50 receives the output sub(x, y) from the difference extractor 49, and the outputs thL(x, y), thH(x, y) from the threshold calculator 48, and decides if the following expression is satisfied.

$$thL(x,y) \leq sub(x,y) \leq thH(x,y) \quad (28)$$

That is, if the above condition is satisfied, the pixel at (x, y) is decided not to be defective. If it is not satisfied, the pixel at (x, y) is decided to be defective. The defect decision circuit 50 thus produces a def(x, y) of 0 for the non-defective pixel or 1 or above for the defective pixel.

A feature extractor 50a makes noise removal process (for example, reduces/expands the def(x, y)), thereby eliminating noise output, and then makes merging process for the neighboring defective pixels. Thereafter, it calculates amounts of various features such as the center-of-mass coordinates, XY projection length and area for each lump.

The whole controller 104 converts the coordinates of the defective part into a coordinate system on the sample, thereby removing false defects, and finally collects defect data formed of position and amounts of features on the sample.

The defect data can be displayed or produced through the output means in the same way as in the embodiment 1.

In addition, the image before gradation conversion or image data and the image after gradation conversion or image data are displayed or the image after gradation conversion or image data are displayed so that the operator can visually confirm that the gradation conversion is properly made for inspection.

According to this embodiment, since the total shift of a small region, very small shift of each pattern edge and a minute gradation difference can be allowed, a correct part can be prevented from being recognized as defect by mistake. Moreover, the allowance of shift and gradation change can be easily controlled by parameters aa, bb, γ and ϵ.

Embodiment 3

Figure 26:
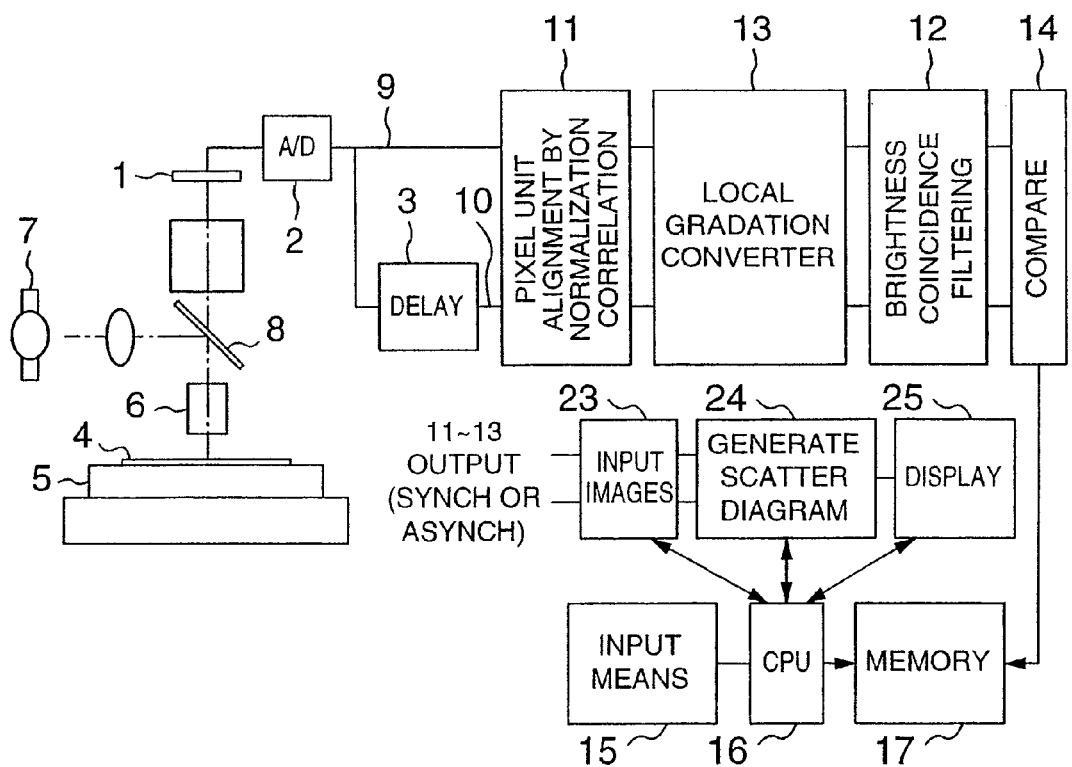
FIG. 26 is a block diagram of a pattern defect inspection apparatus according to another embodiment of the invention.

FIG. 26 shows the third embodiment of a pattern defect inspection method and apparatus according to the invention. Referring to FIG. 26, in which like elements corresponding to those in FIGS. 7 and 8 are provided, there are shown the image sensor 1 for producing a gradation image signal according to the brightness, or gradation of the reflected light from the semiconductor wafer 4 that has patterns being inspected, the A/D converter 2 for converting the gradation image signal from the image sensor 1 into the digital image signal 9, the delay memory 3 for delaying the gradation image signal, the semiconductor wafer 4 having the patterns being inspected, and the stage 5 on which the semiconductor wafer 4 of the patterns being inspected is placed and which is moved in the X-direction, Y-direction, Z-direction and θ-direction (rotation). In addition, there are shown the object lens 6 placed facing to the semiconductor wafer 4, the light source 7 for illuminating the semiconductor wafer 4 of the patterns being inspected, the half mirror 8 for reflecting the illumination light to permit the light to pass through the object lens 6 and illuminate the semiconductor wafer 4, and at the same time allowing the reflected light from the semiconductor wafer 4 to transmit therethrough, and the digital image signal 9 produced from the A/D converter.

Thus, the illumination light from the light source 7 is reflected and passed through the object lens 6 to illuminate the semiconductor wafer 4, or making, for example, bright filed illumination to the wafer.

The delay memory 3 may be a memory for storing and delaying a pitch of one cell or a plurality of cells repeated, of the image signal 9 or may be a delay memory for storing and delaying a pitch of one chip or a plurality of chips repeated, of the image signal 9.

The block 11 is used to align the digital image signal 9 and the delayed digital image signal 10. In this embodiment, it detects the amount of shift at which the gradation difference between pixels is the minimum by normalization correlation, and causes one image to shift on the basis of this amount of shift so that the two images can be aligned. The normalization is made in order to reduce the effect of the brightness difference between the images being aligned.

In other words, the stored image g(x, y) is shifted relative to the detected image f(x, y), and the position at which the correlation value becomes the maximum is estimated from the following equations.

$$R(\Delta x, \Delta y) = \sum_{x=0}^{X-1}\sum_{y=0}^{Y-1} \frac{\{f(x,y)-\overline{f}\}\left\{\begin{array}{c}g(x+\Delta x, y+\Delta y) - \\ \overline{g}(\Delta x, \Delta y)\end{array}\right\}}{\sqrt{f\sigma \cdot g\sigma(\Delta x, \Delta y)}} \quad (29)$$

$$\overline{f} = \frac{1}{XY}\sum_{x=0}^{X-1}\sum_{y=0}^{Y-1} f(x,y) \quad (30)$$

$$\overline{g}(\Delta x, \Delta y) = \frac{1}{XY}\sum_{x=0}^{X-1}\sum_{y=0}^{Y-1} g(x+\Delta x, y+\Delta y) \quad (31)$$

$$f\sigma = \sum_{x=0}^{X-1}\sum_{y=0}^{Y-1} \{f(x,y)-\overline{f}\}^2 \quad (32)$$

$$g\sigma(\Delta x, \Delta y) = \sum_{x=0}^{X-1}\sum_{y=0}^{Y-1} \{g(x+\Delta x, y+\Delta y)-\overline{g}(\Delta x, \Delta y)\}^2 \quad (33)$$

Here, although the image is continuously detected by the image sensor, the detected image is divided into lines as will be described later, and the alignment is performed for line units. In the above equations, the detected image has a size of X×Y pixels.

Although not shown, the normalization correlation for use in finding the image shift need not be made for all image, but may be performed for, for example, small information-carrying images of K small parts (size of X/K×Y pixels) into which a picture is divided in the longitudinal direction of the image sensor.

The decision of whether there is information is made by, for example, differentiating each small image to detect the presence or absence of an edge, and selecting a small image having many edges. If the image sensor is a linear image sensor of multi-tap structure capable of parallel outputs, the image from each tap output corresponds to the small image. This idea is based on the fact that the images from the parallel outputs have an equal shift. In addition, the image sensor used here may be an TDI, CCD image sensor of time delay integration type.

The gradation converter 13 converts the gradations of both image signals having a different brightness in order to make the brightness values equal. Here, linear conversion is performed for each pixel by gain and offset to achieve the brightness matching.

$$\sum_{x=-dx}^{dx} \sum_{y=-dy}^{dy} W(x, y, dx, dy) \cdot \left( \frac{f(x, y) - a(x, y) \cdot}{g(x, y) - b(x, y)} \right)^2 \quad (34)$$

$$W(x, y, dx, dy) = \max\left[ 1 - \left( \frac{f(x, y) -}{g(x+dx, y+dy)} \right)^2 \Big/ D^2, 0 \right] \quad (35)$$

$$a(x, y) = \frac{\left\{ \sum_{x=-dx}^{dx} \sum_{y=-dy}^{dy} \left( W\binom{x, y,}{dx, dy} \cdot f(x, y) \cdot g(x, y) \right) - \frac{1}{\sum_{x=-dx}^{dx} \sum_{y=-dy}^{dy} W\binom{x, y,}{dx, dy}} \cdot \sum_{x=-dx}^{dx} \sum_{y=-dy}^{dy} \left[ W\binom{x, y,}{dx, dy} \cdot f(x, y) \cdot \right] \sum_{x=-dx}^{dx} \sum_{y=-dy}^{dy} \left[ W(x, y) \cdot g(x, y) \right] \right\}}{\left\{ \sum_{x=-dx}^{dx} \sum_{y=-dy}^{dy} \left( W\binom{x, y,}{dx, dy} \cdot g(x, y) \cdot g(x, y) \right) - \frac{1}{\sum_{x=-dx}^{dx} \sum_{y=-dy}^{dy} W\binom{x, y,}{dx, dy}} \cdot \sum_{x=-dx}^{dx} \sum_{y=-dy}^{dy} \left[ W\binom{x, y,}{dx, dy} \cdot g(x, y) \cdot \right] \sum_{x=-dx}^{dx} \sum_{y=-dy}^{dy} \left[ W(x, y) \cdot g(x, y) \right] \right\}} \quad (36)$$

$$b(x, y) = \frac{\left\{ \sum_{x=-dx}^{dx} \sum_{y=-dy}^{dy} \left( W\binom{x, y,}{dx, dy} \cdot f(x, y) \right) - a(x, y) \cdot \sum_{x=-dx}^{dx} \sum_{y=-dy}^{dy} \left( W(x, y, dx, dy) \cdot g(x, y) \right) \right\}}{\sum_{x=-dx}^{dx} \sum_{y=-dy}^{dy} W(x, y, dx, dy)} \quad (37)$$

The converter 12 coverts both image signals having a different brightness in order to make the brightness values coincident. In this embodiment, filtering operation is performed for all images to achieve the brightness matching.

The produced image signals are compared by the comparator 14. An inconsistency, if present, is detected as a defect.

An image input unit 23 receives two images being compared. The input images are supplied to a scatter diagram generator 24, which then produces a scatter diagram. The scatter diagram shows the brightness values of the two images on the ordinate and abscissa. The display 25 indicates the produced scatter diagram. The input means 15 inputs, for example, a threshold for the binary conversion of the absolute value of a difference image, and plots a line segment of the inputted threshold on the scatter diagram. Thus, whether the input threshold is appropriate or not can be decided easily by observing this scatter diagram. Also, with reference to the displayed scatter diagram, it is possible to determine a threshold suitable for the images. One example of the scatter diagram will be shown in FIG. 33.

When W(x, y, dx, dy)=1, the following equations can be satisfied.

$$a(x, y) = \frac{\left\{ \sum_{x=-dx}^{dx} \sum_{y=-dy}^{dy} \left( \frac{f(x, y) \cdot}{g(x, y)} \right) - \frac{1}{(2dx+1) \cdot (2dy+1)} \cdot \sum_{x=-dx}^{dx} \sum_{y=-dy}^{dy} \cdot f(x, y) \cdot \sum_{x=-dx}^{dx} \sum_{y=-dy}^{dy} g(x, y) \right\}}{\left\{ \sum_{x=-dx}^{dx} \sum_{y=-dy}^{dy} \left( \frac{g(x, y) \cdot}{g(x, y)} \right) - \frac{1}{(2dx+1) \cdot (2dy+1)} \cdot \sum_{x=-dx}^{dx} \sum_{y=-dy}^{dy} \cdot g(x, y) \cdot \sum_{x=-dx}^{dx} \sum_{y=-dy}^{dy} g(x, y) \right\}} \quad (38)$$

$$b(x, y) = \frac{\left\{ \sum_{x=-dx}^{dx} \sum_{y=-dy}^{dy} \left( \frac{f(x, y) -}{a(x, y)} \right) \cdot \sum_{x=-dx}^{dx} \sum_{y=-dy}^{dy} (g(x, y)) \right\}}{(2dx+1) \cdot (2dy+1)} \quad (39)$$

In addition, a line segment is applied to the plotted data group on the scatter diagram by means of the method of least squares, and error can be found as the deviation from this line segment.

If a straight line is expressed by Y=m·f(x, y)+n, the least squares (m, n) can be linearly approximated by the following equations.

$$m = \frac{\sum_{x=-dx}^{dx} \sum_{y=-dy}^{dy} \left( \frac{f(x, y) \cdot}{g(x, y)} \right) - \frac{\sum_{x=-dx}^{dx} \sum_{y=-dy}^{dy} f(x, y) \sum_{x=-dx}^{dx} \sum_{y=-dy}^{dy} g(x, y)}{(2dx+1) \cdot (2dy+1)}}{\sum_{x=-dx}^{dx} \sum_{y=-dy}^{dy} f(x, y)^2 - \frac{\left( \sum_{x=-dx}^{dx} \sum_{y=-dy}^{dy} f(x, y) \right)^2}{(2dx+1) \cdot (2dy+1)}} \quad (40)$$

$$n = \overline{g(x, y)} - m \cdot \overline{f(x, y)} \quad (41)$$

The error from the straight line is estimated from, for example, the following equations.

$$Vr = \frac{1}{(2dx+1) \cdot (2dx+1) - 1} \sum_{x=-dx}^{dx} \sum_{y=-dy}^{dy} \left( \frac{m \cdot f(x, y) + n -}{(m \cdot \overline{f(x, y)} + n)} \right)^2 \quad (42)$$

$$= \frac{1}{(2dx+1) \cdot (2dx+1) - 1} \sum_{x=-dx}^{dx} \sum_{y=-dy}^{dy} \left( m \cdot \left( \frac{f(x, y) -}{\overline{f(x, y)}} \right) \right)^2$$

$$Ve = \frac{1}{(2dx+1) \cdot (2dx+1) - 2} \sum_{x=-dx}^{dx} \sum_{y=-dy}^{dy} \left( \frac{g(x, y) -}{(m \cdot f(x, y) + n)} \right)^2 \quad (43)$$

Figure 27:
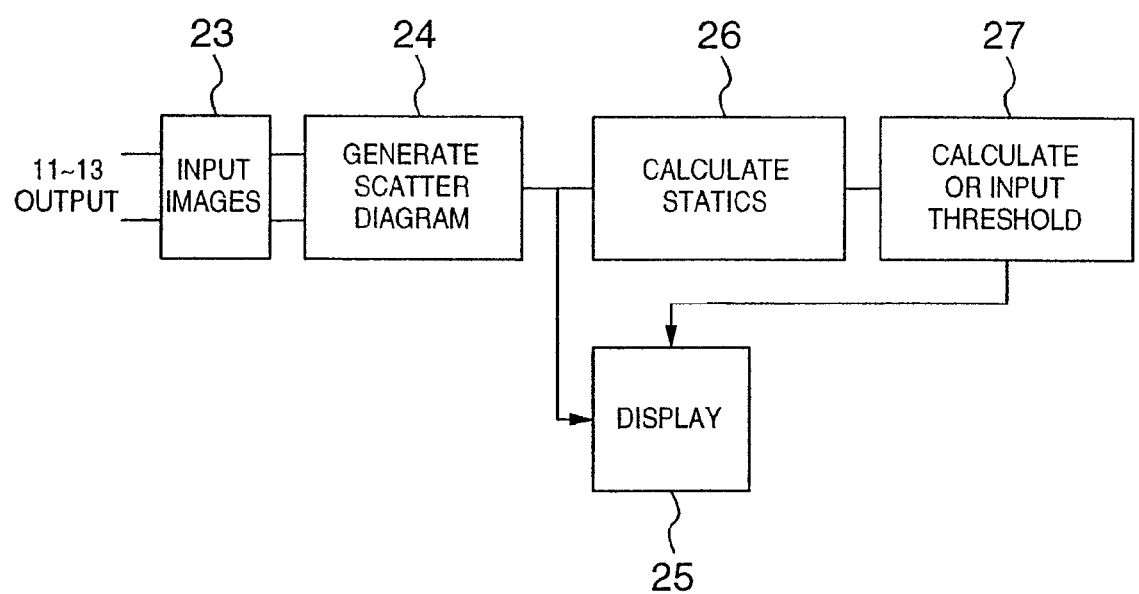
FIG. 27 is a diagram to which reference is made in explaining the scatter diagram production 24 and display 25 according to the embodiment of the invention.

The threshold is calculated on the basis of this error, and can be plotted on the scatter diagram. For example, the threshold is a value proportional to the square root of this Ve. FIG. 27 illustrates an example of the structure for this.

A statistics calculator 26 makes the application to the line segment and calculation of error from the segment. A threshold calculator 27 computes a threshold from the produced statistics. Of course, an arrangement may be provided by which the user can input a threshold.

The images to be used on the scatter diagram are two images being compared, for example, images of pixel units after alignment. At each step of the image processing, two images can be supplied to the image input unit 23.

Figure 28:
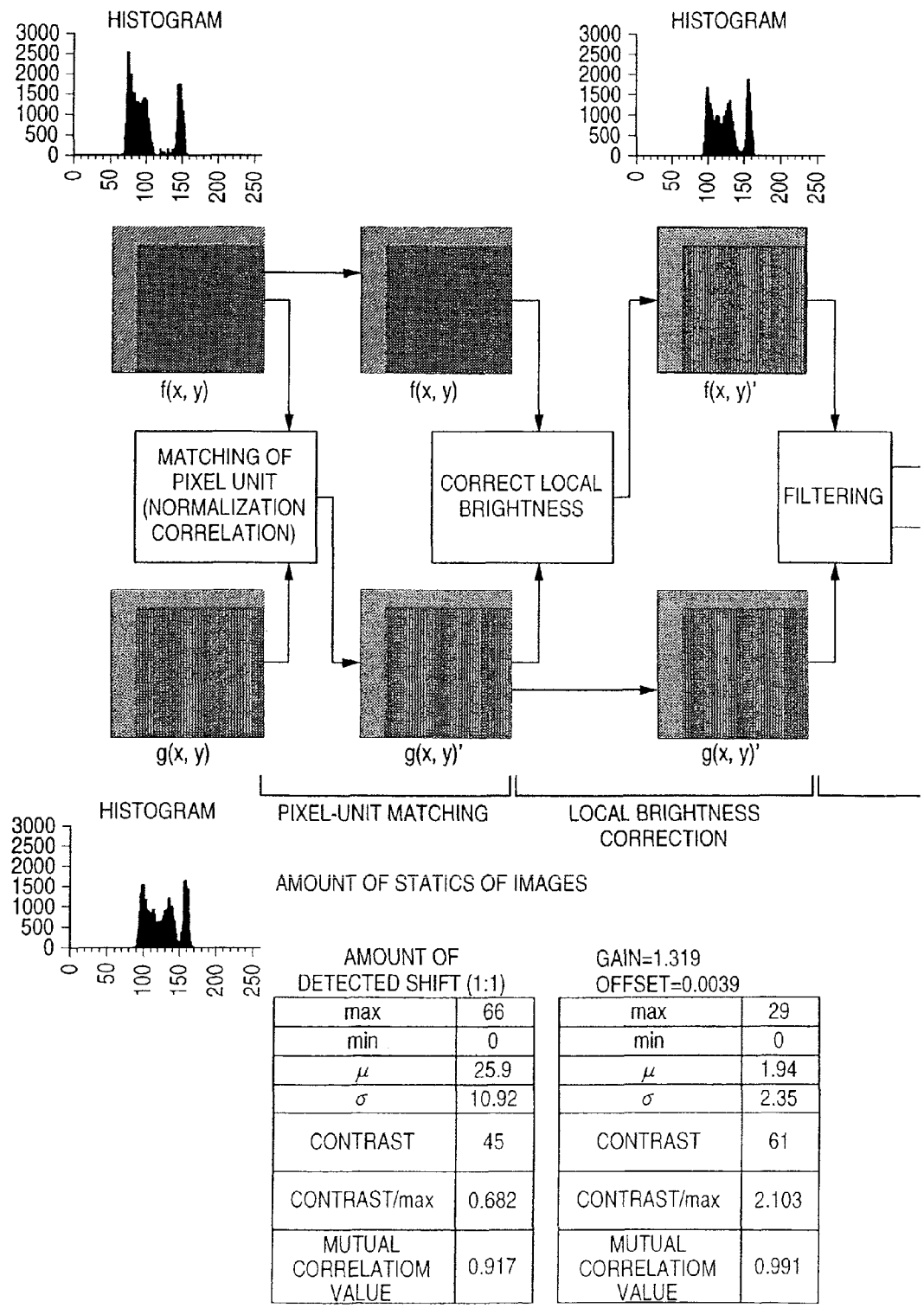
FIGS. 28 and 29 are diagrams showing the results at each image processing on two pictures being compared.
Figure 29:
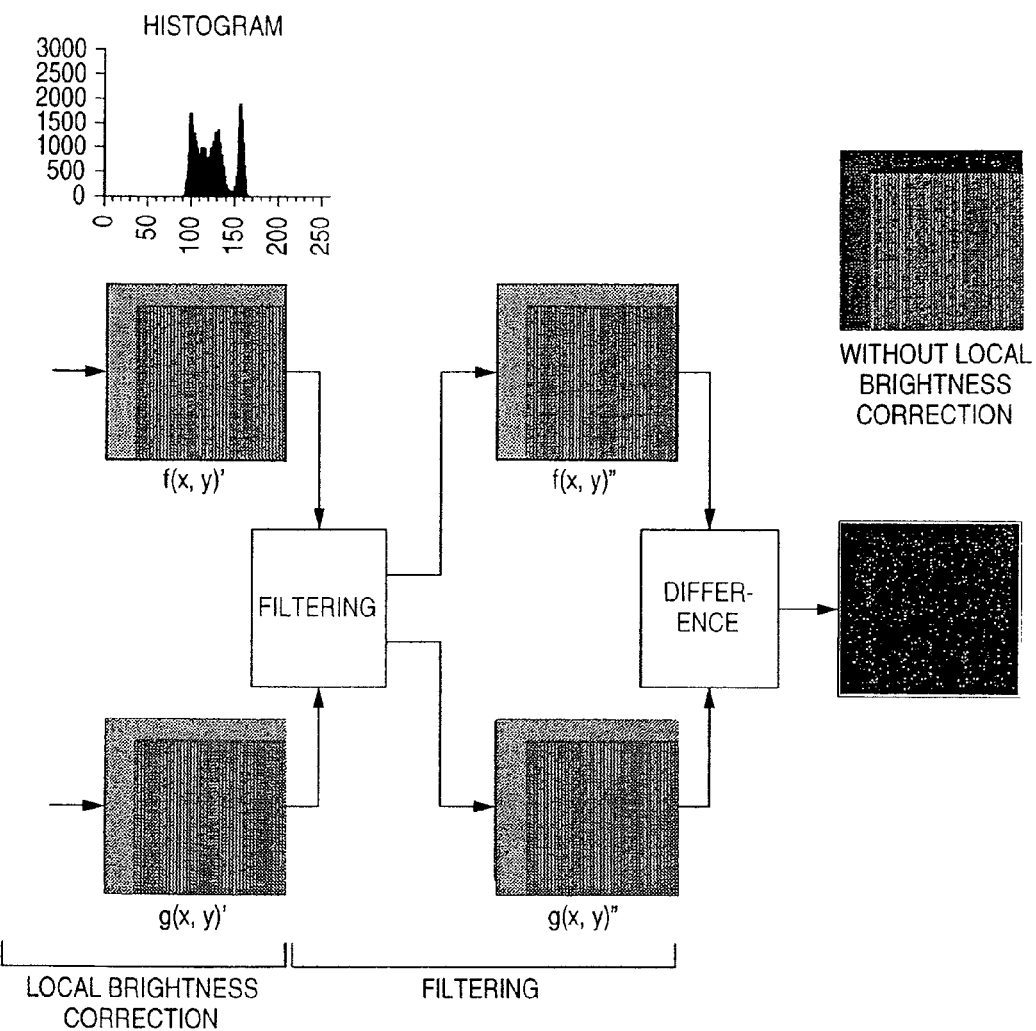

FIGS. 28 and 29 show examples of two images processed according to the system illustrated in FIG. 26. A pattern of lines and spaces is detected on the lower right region of the images. The upper left region has no pattern. FIGS. 28 and 29 also show histograms of images in the course of each process, and statistics of different image. From the histograms, it will be seen that the brightness values of two images are not coincident at the first step.

First, a correlation value is estimated from the normalization correlation, the position at which this correlation value is high is found, and alignment is performed with an accuracy of pixel unit. Then, the two images aligned are subjected to local brightness correction that is local gradation conversion. Finally, filtering is made to permit the two images to coincide in brightness, thereby further increasing the degree of coincidence in the image brightness.

FIGS. 30~32 show scatter diagrams of images at each step of process. Since the two images are not coincident in brightness at the stage where the images are aligned with an accuracy of pixel units, the values scatter out of the straight line of 45-degrees gradient on the scatter diagrams. However, after the local gradation conversion, or local brightness correction, and filtering process according to the invention, the values are distributed around the straight line on the scatter diagram. Thus, from the scatter diagrams it will be understood that there is an effect of making the brightness values of the two images uniform. The gradient and intercept in the figures are the gradient and intercept of a line segment fitted to the data of scatter diagrams.

The gradient as the scale for the degree of coincidence between the two images was first 0.705, changed to 0.986 after the local gradation conversion, or local brightness correction, and arrived at 0.991 after the filtering process. Thus, it will be understood that the degree of coincidence between brightness values is improved.

Moreover, the value of Ve indicating the degree of coincidence between the two images was first 40.02, changed to 8.598 after the local gradation conversion, or local brightness correction, and reached 7.477 after the filtering process. Thus, the degree of brightness coincidence is increased. The Ve value is not of all image, but is, for example, a linearly approximated error Ve of each region of 7×7 pixels including the surroundings of each pixel as illustrated in FIGS. 30~32. From the images, where the brightness matching error is large will be seen.

FIGS. 21~23 show scatter diagrams of local contrast of images. In this embodiment, the contrast is the difference between the maximum and minimum of the surroundings of each pixel, or for example 3×3 pixels. The local contrast after the local gradation conversion and filtering process according to the invention is distributed scatting near the straight line on the scatter diagrams. The gradient and intercept have the same meaning as in the previously given diagrams. The images of Ve values are of linearly approximated Ve for a region of 7×7 pixels including the surroundings of each pixel in the local contrast image.

Figure 33:
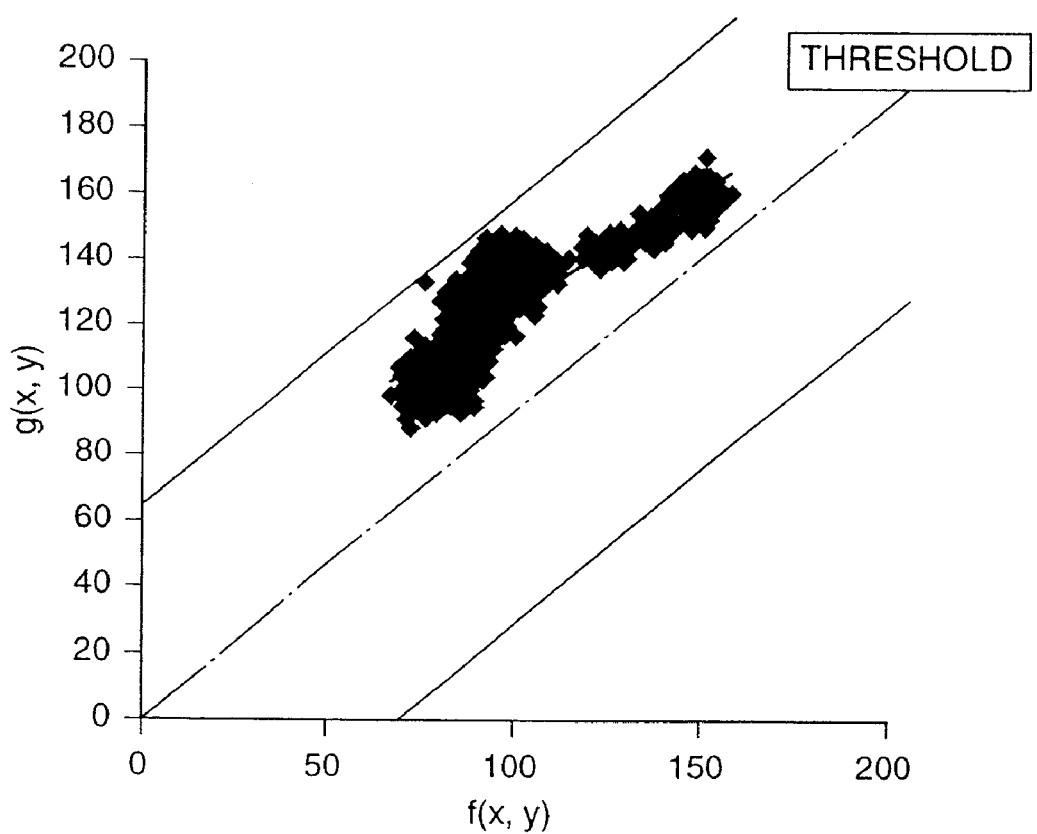
FIGS. 33-37 are examples of scatter diagrams.
Figure 34:
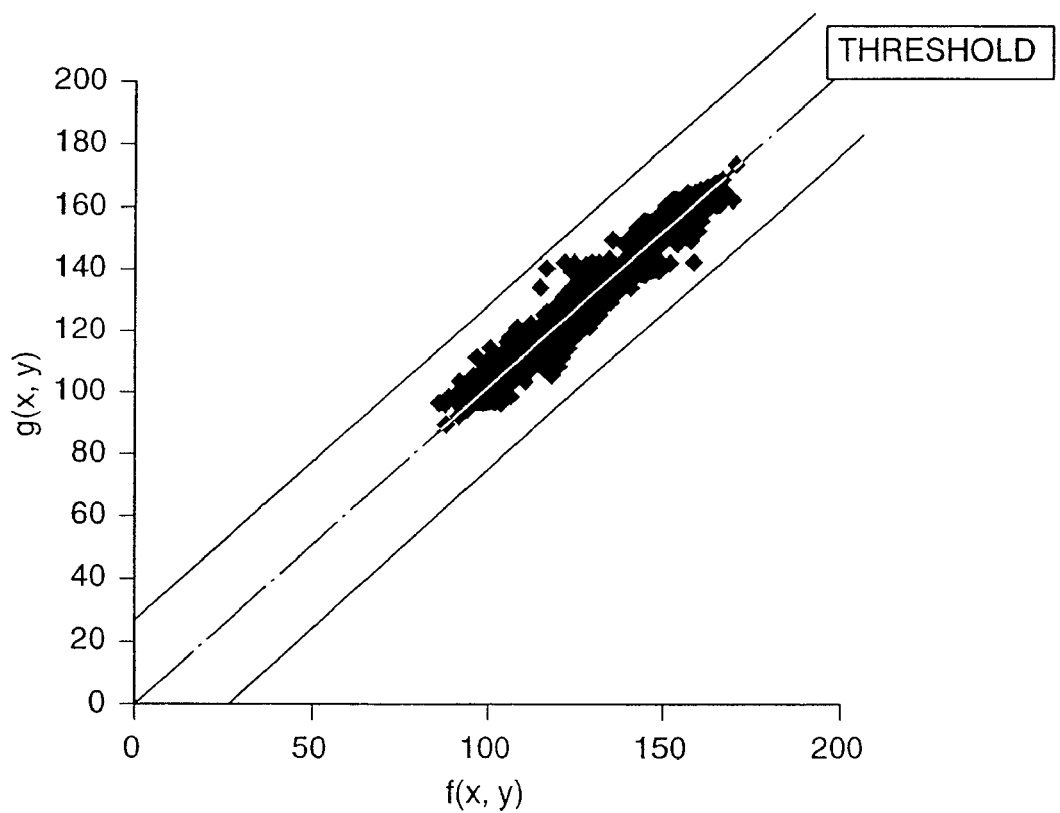
Figure 35:
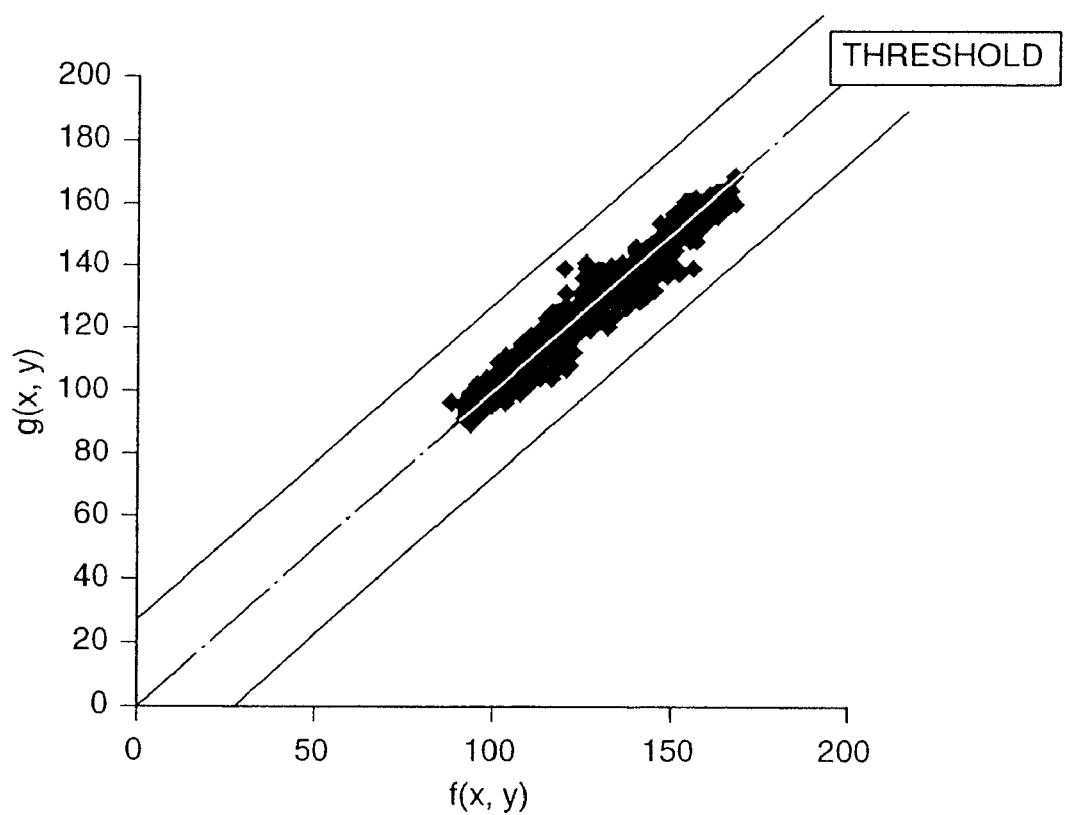
Figure 36:
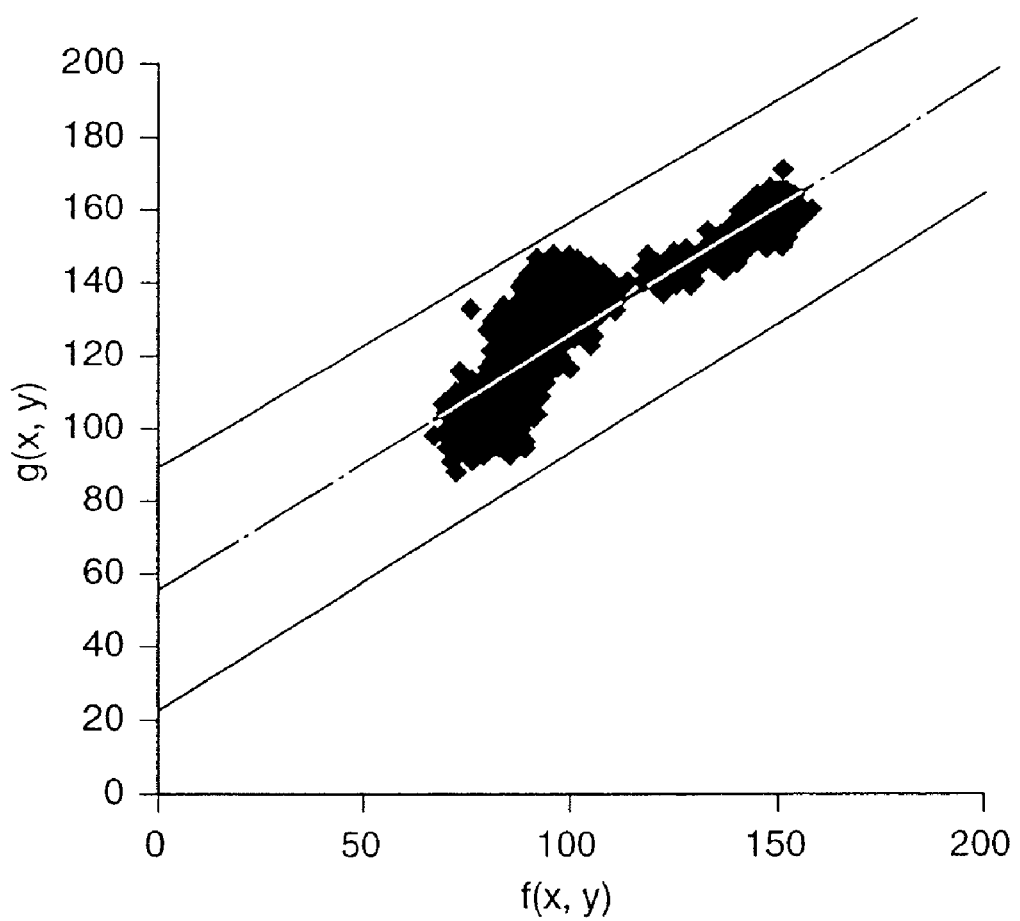

FIGS. 33~36 show examples of scatter diagrams and thresholds. In FIG. 33, since two images are different, the threshold is set to be large for preventing the erroneous detection of the images. FIG. 34 is a scatter diagram after the local gradation conversion, or brightness correction according to the invention. Since the degree of coincidence between the two images is high, the set threshold is small. FIG. 35 is a scatter diagram after the brightness coincidence. The threshold is further reduced. FIG. 36 is a scatter diagram after the linear gradation conversion of one image for image unit not each pixel unit. The threshold has an offset on the scatter diagram.

Figure 37:
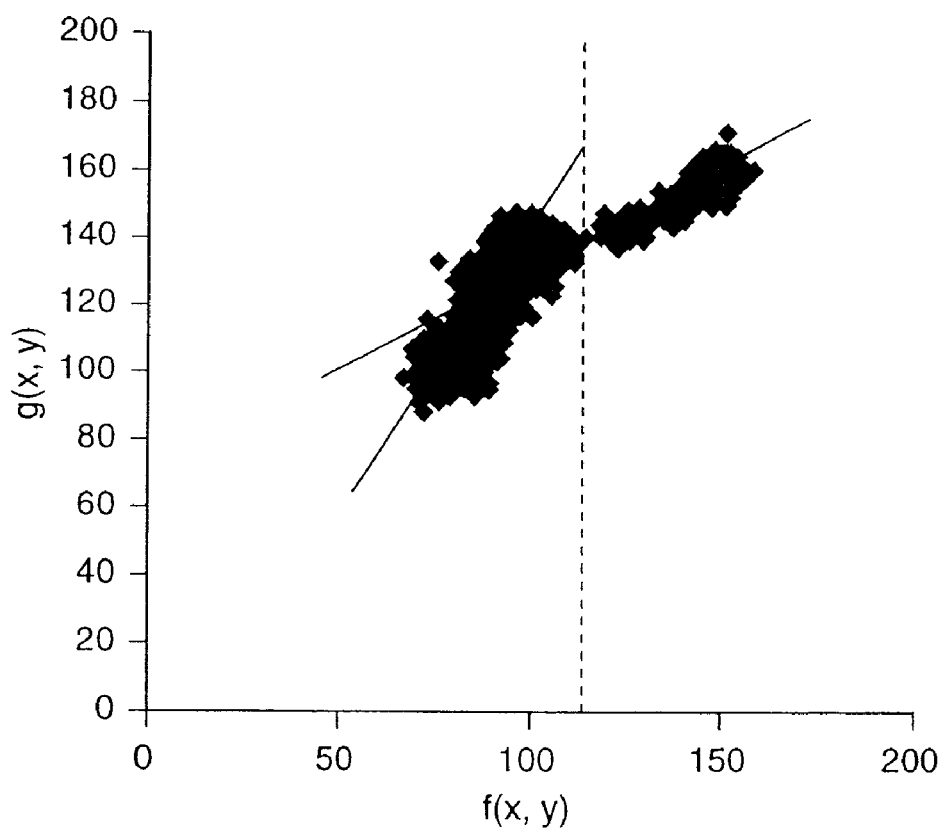

FIG. 37 shows an example of divisional linear gradation conversion for image unit. In this example, two divisions are shown.

The scatter diagram and threshold can be widely used for the standard to determine a defect detection sensitivity or for the confirmation of if the established threshold is appropriate.

The generation and display of these scatter diagrams or the calculation of threshold using data of the scatter diagrams can be performed by using images detected before the start of inspection. In addition, it will be clear that if the generation of scatter diagrams and threshold setting are carried out for each image in synchronism with the image detection, the inspection can be conducted with high sensitivity. The image detection may be made after the completion of the respective processes. While the image process is achieved by the pipeline type process as described above, it may be made by another arrangement.

Embodiment 4

Figure 38:
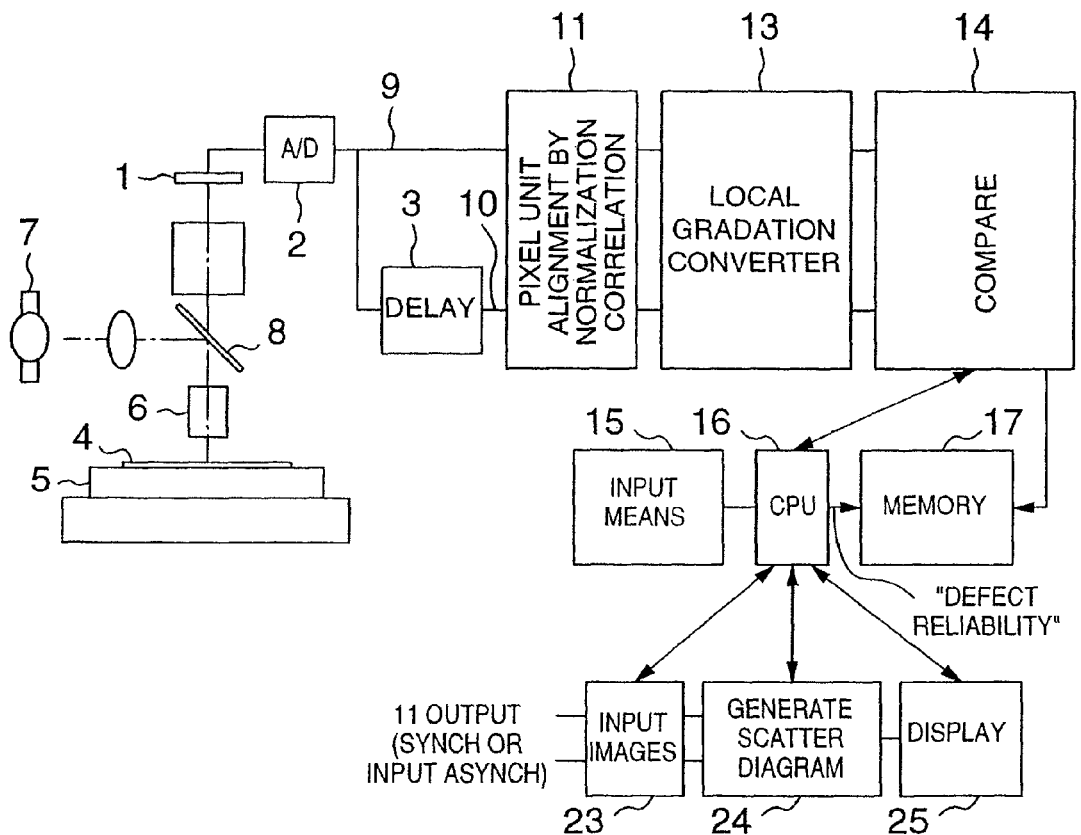
FIG. 38 is a partially cross-sectional block diagram of a pattern defect inspection apparatus according to still another embodiment of the invention.
Figure 41:
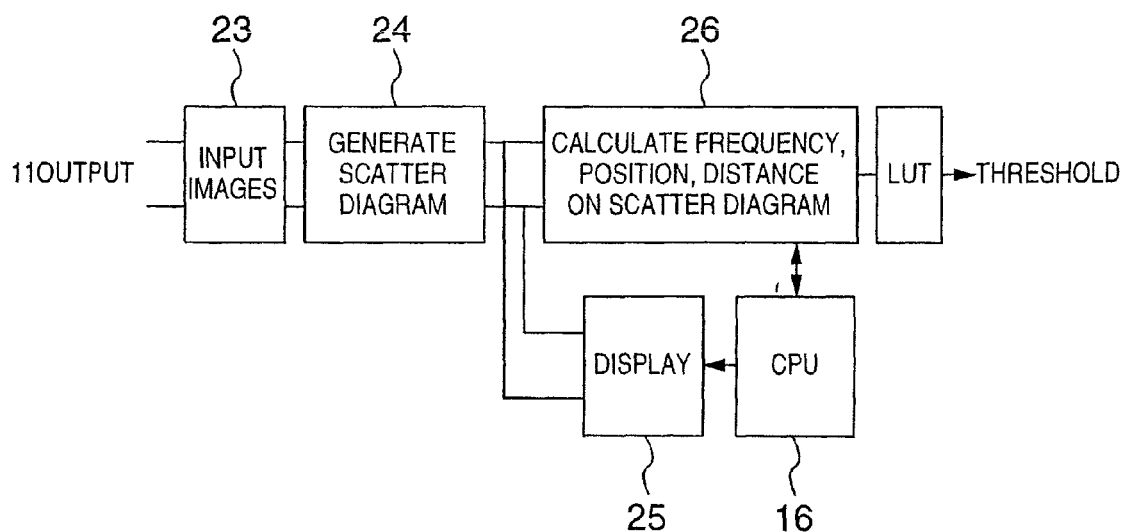
FIG. 41 is a block diagram to which reference is made in explaining the scatter diagram production and display according to the embodiment of the invention.

FIG. 38 illustrates the fourth embodiment of a pattern defect inspection method and apparatus according to the invention.

The construction shown in FIG. 38 is the same as that of FIG. 26 except for the image brightness coincidence filter 12. In FIG. 38, like elements corresponding to those in FIG. 26 are identified by the same reference numerals.

The operation of the arrangement shown in FIG. 38 is the same as in the third embodiment in that the image sensor 1 generates a gradation image signal according to the brightness of the reflected light from the semiconductor wafer 4 of patterns being inspected, and that the local gradation converter 13 makes linear conversion by gain and offset for each pixel, thereby achieving brightness coincidence.

In this embodiment, the comparator 14 compares the image signals produced from the local gradation converter 13, thereby detecting an inconsistency as a defect. The detected image signal undergoes constant sequential processes of pipeline type, and finally the defect and its features are produced.

The operation of the inspection apparatus having the above construction will be described below.

Referring to FIG. 38, the illumination light focused by the object lens 6 scans the stage 5 in the X direction (for example, in the direction perpendicular to the array direction of sensor chips on the sensor surface of the on-dimensional image sensor 1) while the stage 5 is being moved at a uniform speed so that a necessary region of the semiconductor wafer 4 having patterns being inspected can be scanned by the illumination light. Consequently, the image sensor 1 detects the brightness information (gradation image signal) of the memory mats 21 and peripheral circuits 22 within the pattern formed on the semiconductor wafer 4, or within the chip 20.

When the stage completes the movement of one row, it fast moves in the Y-direction (perpendicular to the X-direction) to reach the start point of the next row. In other words, while the image sensor 1 detects the image of the pattern formed on the semiconductor wafer 4, the stage 5 repeats the uniform movement along a row and fast movement for the start of the next row. Of course, the step and repeat type inspection may be employed.

The A/D converter 2 converts the output (gradation image signal) from the image sensor 1 into the digital image signal 9. This digital image signal 9 is of 10 bits. Of course, if it has about 6 bits, it can be well processed without problem. However, in order to detect a very small defect, the number of bits is required to be large to some extent. Thus, here a ten-bit format is used for somewhat margin.

Referring to FIG. 38, the coordinates of array data within the chip on the semiconductor wafer 4 that are obtained on the basis of the design information are inputted by the input means formed of a keyboard or disk. The CPU 16 generates defect inspection data according to the inputted coordinates of the array data within the chip on the semiconductor wafer 4, and causes it to be stored in the memory 17. The defect inspection data stored has also data of defect reliability added indicating the certainty of defect which will be described later.

This defect inspection data, if necessary, can be displayed on display means or printed out by output means such as a printer together with the defect reliability. The defect inspection data and defect reliability can be transmitted by communication equipment to other inspection apparatus, optical review apparatus, SEM type review apparatus or defect classification apparatus (there are various different apparatus such as apparatus for classifying defect features into defect categories, and apparatus used in a neural network) or to external storage means such as a server. Of course, only the defect reliability may be displayed, printed out or supplied to other means.

The image input unit 23 is used to input two images being compared. These images are supplied to the scatter diagram generator 24, which then produces a scatter diagram. FIG. 39 shows how to generate the scatter diagram. The ordinate and abscissa in the scatter diagram indicate the two images f(x, y), g(x, y) being compared, respectively. The scatter diagram may show the local contrast of brightness or local average or a combination thereof on the ordinate and abscissa except the brightness of image signals of patterns being inspected. The generated scatter diagram is displayed with the frequency converted into gradation values as illustrated in FIG. 39. Here, the frequency of 0 is indicated by gray, low frequency by white, and high frequency by black. Of course, the scatter diagram may illustrate only the presence or absence of data.

The calculator 26 calculates the frequency on the scatter diagram, function of position or relative distance on the scatter diagram or information referring to a look-up table from the above scatter diagram of image signals. The calculated information is added to the inconsistency information as defect reliability or as a scale for the inconsistency corresponding to a defect, and stored in the memory 17.

Here, a high frequency in the scatter diagram indicates that the corresponding point is unlike defect. For example, the pixel corresponding to the black data on the scatter diagram in FIG. 39 has a high frequency, and hence it seems a normal portion with a high probability. The pixel corresponding to white data has a low frequency and only a fraction of brightness, and hence it is a defect with a high probability. Thus, the frequency information is an important parameter for indicating the certainty of defect. Similarly, if the brightness values of two images being compared are equal, those points are distributed on a straight line having a gradient of 45 degrees on the scatter diagram. Therefore, the absolute positions on the scatter diagram are also an important parameter for indicating the certainty of defect. The pixels corresponding to data deviating out of the straight line having a gradient of 45 degrees (not shown) have low frequencies, and thus they can be considered most probably as defects.

Figure 40A:
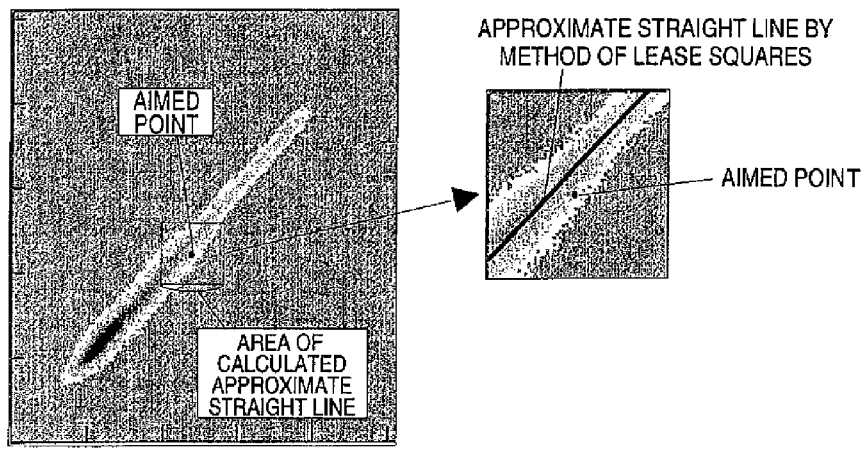
FIGS. 40A and 40B are diagrams to which reference is made in explaining the local gradation conversion according to the embodiment of the invention.
Figure 40B:
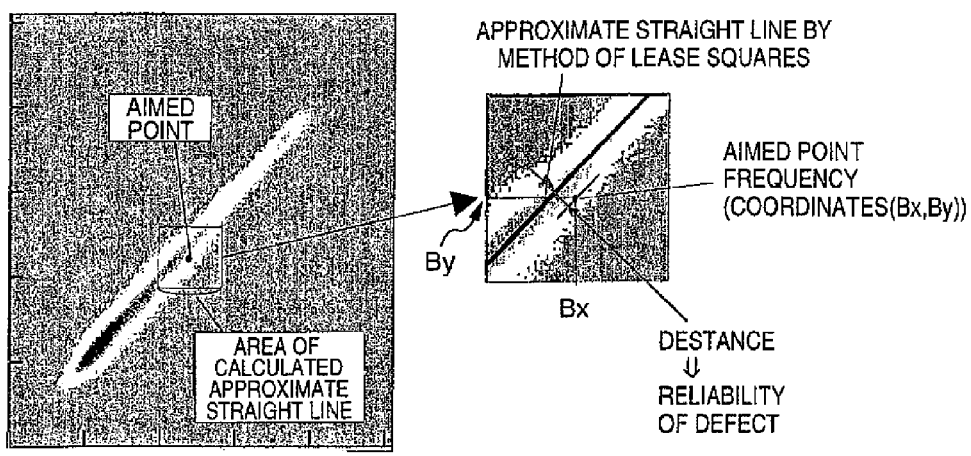

FIGS. 40A and 40B show straight lines estimated by the method of weighted least squares using complex pixels in the area around each aimed point. The relative distances of two images being compared are the distances from the straight lines.

As illustrated in FIG. 40A, an approximate straight line is estimated relative to the data within an area set around each pixel on the scatter diagram. Alternatively, a straight line of weighted least squares of two images being compared is estimated by using the fact that the frequency is a parameter for indicating the certainty of defect, or by using complex pixels in an area set around each point where the frequency is a constant or above. The size of the area is locally changed according to the frequency in the scatter diagram. It is flexible and desired to produce the area size by inputting the frequency and referring to the look-up table.

The distance from the approximate straight line is plotted as in FIG. 40B, and this distance is regarded as the certainty of defect, and fed to the outside or displayed. The smaller the distance, the more probably the image can be decided to be normal. The larger the distance, the closer the image is to a defect.

From FIG. 40B, it will be seen that the frequency becomes small as the distance from the approximate straight line increases, thus indicating that the certainty of defect increases. The points where the frequency is a constant or above, for example 1 or below are considered as having a high degree of certainty of defect, and thus removed from the region of the approximate straight line. The local gradation converter 12 in FIG. 38 may estimate an approximate straight line for each pixel by the method shown in FIGS. 40A and 40B and make gradation conversion on the basis of the straight lines.

Moreover, the scattering of all image from the straight line can be computed by the equations (42) and (43) used in the third embodiment.

This information can be used as a scale of the degree of coincidence in all image.

Thus, the certainty of inconsistency information produced from the inspection apparatus can be decided by use of the information obtained from the scatter diagram.

The display 25 displays the generated scatter diagram alone or with other information. The input means 15 is used to input thresholds, for example, a threshold for the binary conversion of the absolute value of a difference image, and the line segment of the inputted threshold is plotted on the scatter diagram. By referring to this scatter diagram, the input threshold can be easily decided to be appropriate or not.

In addition, by referring to the information of the displayed diagram, it is possible to determine a threshold suitable for the image. In other words, if the threshold is determined according to the above-given certainty of defect, defects can be detected with higher reliability. For example, a threshold is determined adequately for each pixel, or according to the frequency in the scatter diagram. The conversion between the frequency and the threshold is performed by using the look-up table (LUT) as illustrated in FIG. 8. The contents of the look-up table, or the way to convert is previously determined before the inspection.

As illustrated in FIG. 38, the images used in the scatter diagram, which are two images being compared, for example, images of pixel units after alignment, can be supplied to the image input unit 23 at each step of the image processing.

Figure 42:
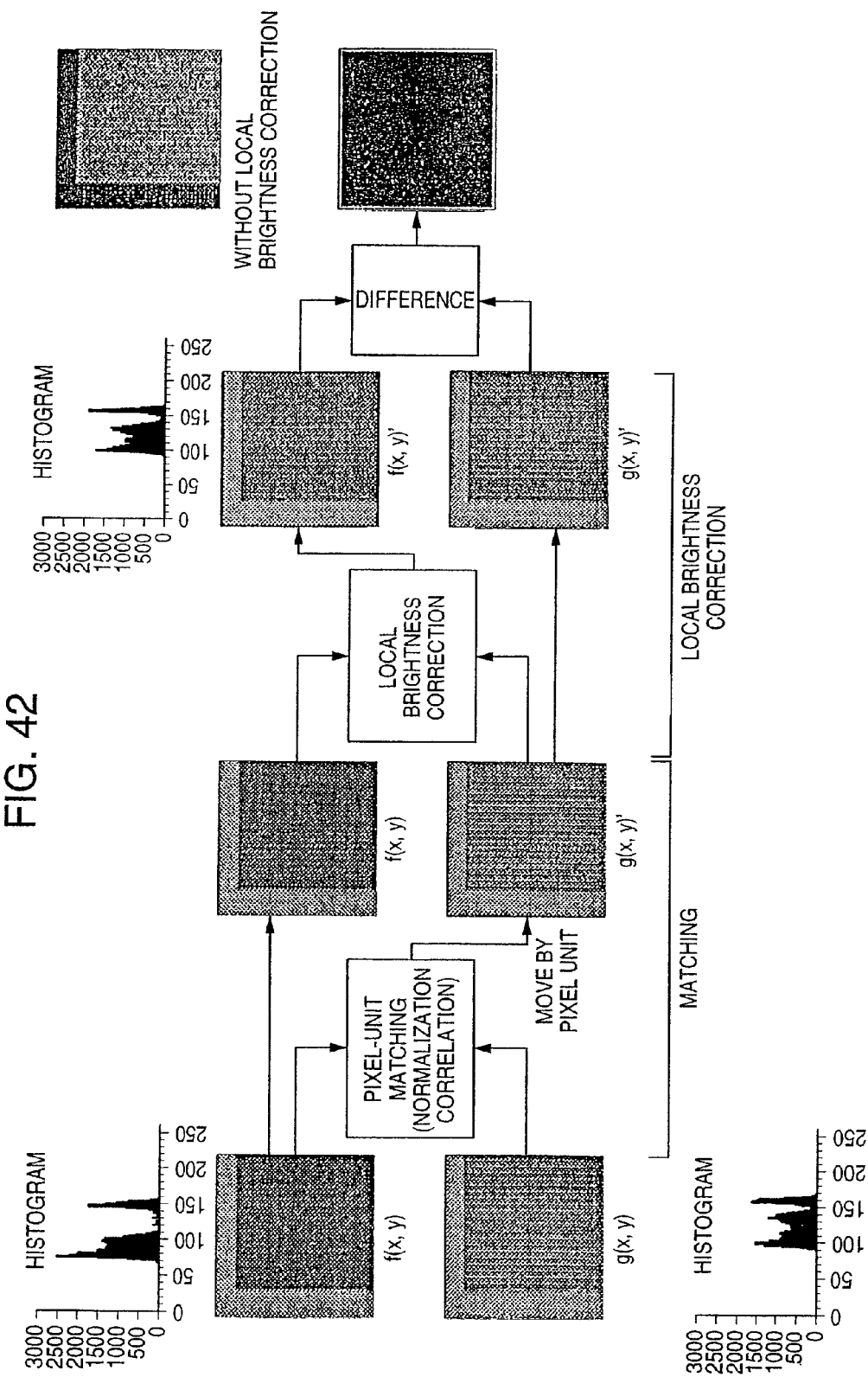
FIG. 42 is a diagram showing the results at each image processing step on two pictures being compared.

FIG. 42 shows an example of the process for the two images based on the system illustrated in FIG. 38. The processed portion is the inspected pattern that has been flattened by CMP (chemical mechanical). The line and space pattern (pattern of a large number of lines arranged with a constant spacing) is detected at the lower right of the image. The upper left region has no pattern. a histogram of images is also shown in the course of each process. From the histograms, it will be seen that at the first stage the brightness values of two images are not coincident. First, the correlation values of the images are estimated by normalization correlation, the position where the correlation value is high is determined, and alignment of images is performed with an accuracy of pixel units. Then, the two aligned images are subjected to local gradation conversion, or local brightness correction.

FIGS. 43A and 43B illustrate scatter diagrams of images. The two images are not coincident in brightness at the stage of alignment with an accuracy of pixel units, and thus become scattering out of a straight line having a gradient of 45 degrees in the scatter diagram. However, after the local gradation conversion process (system based on the equations (34)~(37)) according to the invention, the scatter diagram has a distribution near the straight line. Thus, it will be understood that there is an effect in making the brightness values of two images equal. The gradient and interception are those of a line segment fitted to the data of the scatter diagram.

According to the invention, the gradient as a scale of degree of coincidence between two images is 0.705 at fast and changed to 0.986 after the local gradation conversion, or local brightness correction. Thus, the degree of coincidence between brightness values is increased. The above-mentioned Ve indicating the degree of coincidence between two images is 40.02 at first and changed to 8.598 after the local gradation conversion, or local brightness correction. The degree of coincidence between brightness values is improved.

Although these values are calculated for all images of image units being compared, the above Ve may be estimated for each local size being converted in gradation in the system shown in FIG. 40.

In the examples shown in FIGS. 43A and 43B, information of certainty of defect is added to the inconsistency by using the scatter diagram after the local brightness correction, and according to the above procedure. The pixels distributed around in the scatter diagram have a high degree of certainty of defect. The threshold can be established by using straight lines having a gradient of 45 degrees to put the distributed data therebetween. Of course, even at the stage where images are aligned with an accuracy of pixel units, information of certainty of defect can be similarly extracted from the scatter diagram. However, since the threshold is determined to hold the distributed data therebetween, it cannot be estimated with high sensitivity.

Therefore, for determining a threshold it is more desirable to use a scatter diagram generated after the local brightness correction.

If the generation or display of the scatter diagram or the calculation of thresholds using data of the scatter diagram is performed for each image or each pixel of an image in synchronism with the image detection, the inspection can be made with high sensitivity. While the image processing is of the pipeline type as described above, another type of image processing can be used.

FIGS. 44A~44C show lists of defect output. The values listed are inconsistency outputs resulting from comparing the gradation-converted images by the comparator 14. The lists include the values of defect reliability in addition to the values indicating the defect number and the features of defect such as coordinates, length and area. Here, the defect number indicates the order in which the chips being inspected were scanned. The defect coordinates indicate the position at which a defect of a chip being inspected was detected in a coordinate system with, for example, an alignment mark or origin provided as a reference. The defect lengths are the lengths along the X-axis and Y-axis, respectively. Of course, the lengths along the major axis and minor axis may be calculated.

These units are, for example, microns depending on a necessary precision. The defect reliability is the information obtained from the above-mentioned scatter diagram. For example, the defect reliability is expressed by the frequency and distance from the approximate straight line on the scatter diagram of pixels of a defective image.

FIG. 44A is based on the frequency of a defective image in the scatter diagram. The lower the frequency, the higher the defect reliability value. FIG. 44B is based on the distance from the approximate straight line of a defective image in the scatter diagram. The longer the distance, the higher the defect reliability value. FIG. 44C is based on the position of a defective image in the scatter diagram. The reliability value of the defect is increased as the defect is separated more away from the straight line with a gradient of 45 degrees. Of course, the defect reliability value may have a plurality of factors such as the frequency of a pixel of a defective image and the distance thereof from the approximate straight line on the scatter diagram. If the defect covers a plurality of pixels, the amount of statistic is calculated, such as the average, maximum or median of the frequencies of the pixels. Thus, the inconsistency information with the reliability added can be used for the calculation of fatality of defect.

The fatality of defect is the fatality of defect to the inspected pattern, depending on, for example, the size of defect and the coordinates (region) in which the defect exists. The smaller the pattern size, the higher the fatality of the defect of the same size. If this fatality is used with the reliability, the fatality can be decided with high precision. As a result, the defects of the inspected pattern can be more accurately diagnosed by the processes.

Figure 45:
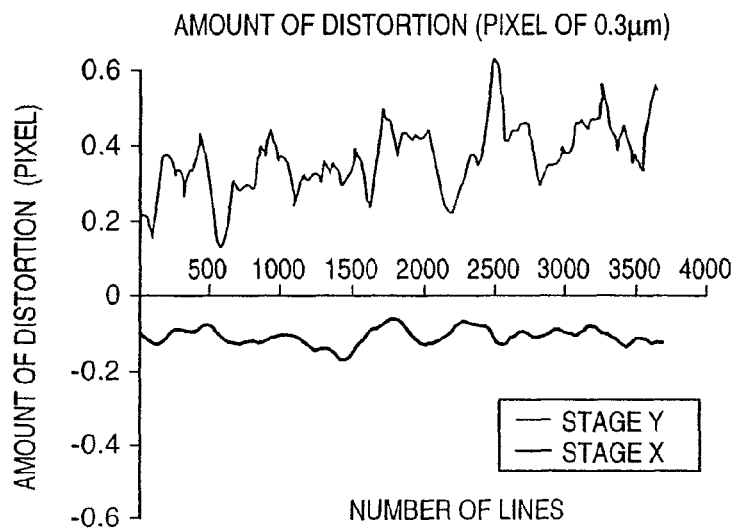
FIG. 45 is a diagram to which reference is made in explaining the amount of positional shift between pictures.
Figure 46:
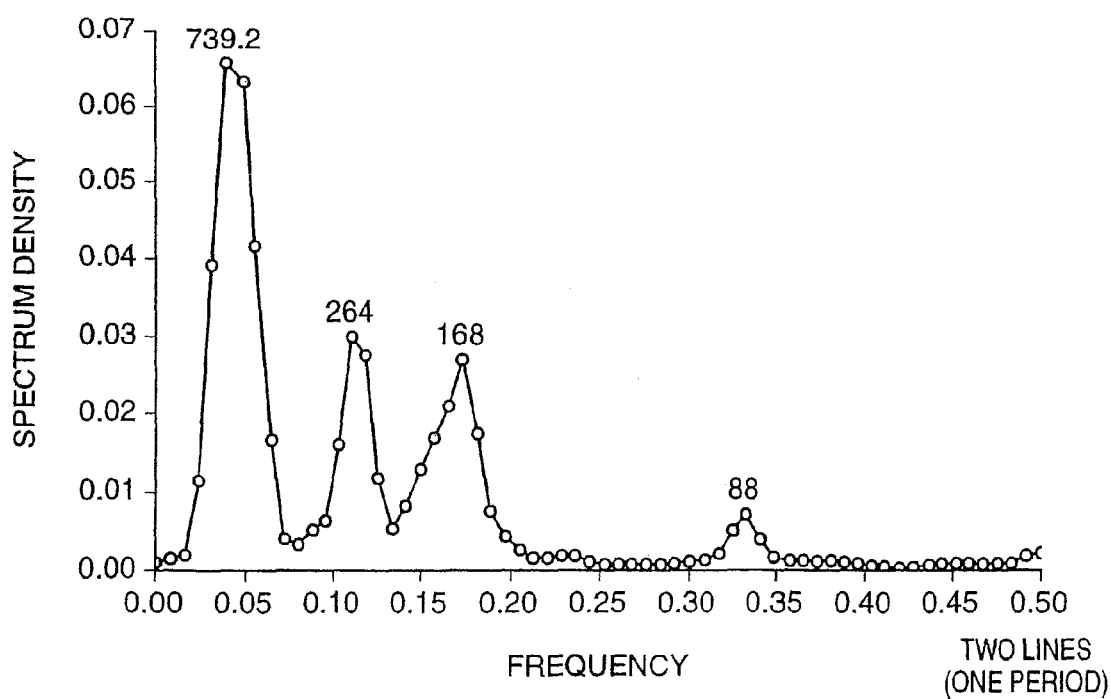
FIG. 46 is a diagram to which reference is made in explaining spectrum analysis.

A supplementary explanation will be made of the size of image. The size of image, or the unit of alignment(matching) of images can be determined by the following method. The amount of shift between two images being compared is estimated in units of fine divisions, as illustrated in FIG. 45. The amount of shift is, as illustrated, detected separately in the X-direction and Y-direction. This shift data can be spectrum-analyzed as shown by the waveform in FIG. 46. In this spectrum-analyzed diagram, the ordinate indicates the spectrum density, and the abscissa the frequency.

In this figure, we consider the highest frequency with high density, or 0.011. This frequency is determined by, for example, apparatus characteristic or vibration characteristic such as the travelling characteristic of the stage. The results of the spectrum analysis indicate that the shift between two images repeats at this frequency. It is now assumed that the reciprocal of this frequency value, or 88 lines is a unit of image, or a unit of matching. If a large peak-to-peak value of shift appears within an image, it is difficult to match both images with high precision. If the unit of image is assumed to be ¼ of the reciprocal of this frequency, the amount of shift can be reduced to ½ of the peak shift or below. In addition, the unit of image is made ⅛ the reciprocal of the frequency, the amount of shift can be reduced to ¼ the peak shift or below.

Thus, as the image unit is decreased to a finer value, the precision of matching between the images should be able to be increased the more. However, the pattern information to be included within the image is decreased, and as a result the image matching precision does not increase. Therefore, from the results of the spectrum analysis the upper limit of the image size can be determined by the necessary matching precision, and from the standpoint of assuring the pattern information the lower limit thereof can be decided by the pattern space information (information of the region with no pattern formed) depending on the patterns being compared. While the highest frequency is considered in the above description, the amount of shift and the frequency corresponding to a large amount of shift may be considered, and in this case effective results can be obtained.

The above process may be made separately for the X-direction and Y-direction or only for the stage movement direction as in the case of an accumulation type linear image sensor.

The size of image at the step of gradation conversion may be made equal to the above-given image size in the system based on the equations (34) and (37) or may be determined locally as in the system mentioned with reference to FIG. 40.

According to the embodiments of the invention, the defects can be detected with high sensitivity without being affected by the change of pattern brightness at different places. In addition, the pattern with the brightness greatly scattering in a dark region such as memory mats 21 can be inspected with high sensitivity. The same effect can be expected not only for the memory elements but for the logic elements in the microcomputer or ASIC. Therefore, high-reliability inspection can be performed as compared with the prior art.

While bright field illumination is employed in the above embodiments, microscope illumination such as dark field illumination or ring band illumination may be used. The illumination used does not depend on the illumination length. In addition, the inspection may naturally use a secondary electron image on the sample surface that can be obtained by detecting the secondary electrons emitted from the sample when an electron beam is irradiated on the sample. Moreover, the inspection may be made a plurality of times with the kind of illumination or the conditions of illumination changed, the results of the inspection being logically summed for the final result. Alternatively, the logical product thereof is used to accurately detect defects. For example, the image defect may be diagnosed by the defect distribution and number. Moreover, the detector is not limited to the linear image sensor, but may be a TV camera by which the pattern image is detected. The kinds of defect may be a defective shape of short-circuit or open-circuit or other foreign bodies.

According to the above embodiments, more effective analyzing processes can be used.

By employing inspection data with reliability added, it is possible to execute review of defects more effectively. For example, in the defect lists shown in FIGS. 44A~44C, the order of defects is changed (sorting) according to the reliability of defects. For example, defects are rearranged in the order of higher certainty of defect. By this arrangement, review of defects and confirmation can be performed in the order of high reliability. It is possible not only to completely prevent the misdetection by the inspection apparatus, but to select the inconsistency on the boundary between the defect and the normal state. If the defect rearrangement is made according not only to the reliability but to the information of coordinates and size of the defects, more effective defect review and confirmation can be performed.

In other words, the decision of fatality can be accurately executed by the addition of reliability, and use of this fatality enables effective defect review and confirmation with higher precision. A threshold may be provided for the reliability or fatality so that only the defects higher than the threshold can be reviewed. Moreover, the same effect can be expected for the classification of defects. In addition, yield diagnosis and prediction can be made without problem by use of only the true defects. Thus, it is possible to reduce the load of the visually reviewing operation for the inconsistency, and increase the reliability of the yield prediction.

While the above embodiments of the invention mentioned above employ the comparative inspection method chiefly using an optical microscope, other scan type electron microscopes or other detectors using infrared light or X-rays may be used with the same effect. In addition, while the above embodiments employ the method based on the comparison between images, the reliability of defects added to the defect information can be applied to the apparatus of such type as foreign body inspection apparatus in which scattered light detects a large area of body without use of comparison.

According to the embodiments 1~4 of the invention, defects can be detected with high sensitivity without being affected by the brightness change of pattern at each position. The pattern of which the brightness greatly scatters in the dark region such as memory mats 21 can be inspected with high sensitivity. Also, high-precision image matching can be performed without being affected by the vibration characteristic of equipment. Therefore, as compared with the prior art, the inspection can be made with high reliability.

The contents of the specifications and drawings of Japanese Patent Application Nos. 110383/1998 and 264275/1998 that are the basic applications for the priority of this application are incorporated in those of this application by this reference.

The invention claimed is:

1. A method of inspecting a specimen, comprising:
  illuminating a specimen, on which plural patterns are formed, with light emitted from a light source;
  capturing a first image of a first area of the specimen in which patterns are formed;
  capturing a second image of a second area of the specimen in which patterns which are essentially the same with the patterns formed in the first area, are formed;
  creating data relating to pixels of the first image and corresponding pixels of the second image, for each pixel;
  determining two thresholds for each pixel for detecting defects directly in accordance with the first image and the second image; and
  detecting defects on the specimen by processing said first image and the second image by using said two thresholds for each pixel,
  wherein the thresholds are determined by using information of brightness of a local region of at least one of the first image and the second image, with the local region including an aimed pixel and peripheral pixels of the aimed pixel.

2. A method of inspecting a specimen according to claim 1, wherein said first image and said second image are both bright field images.

3. A method of inspecting a specimen according to claim 1, wherein said first image and said second image are both dark field images.

4. A method of inspecting a specimen according to claim 1, wherein in the creating operation, said pixel data includes brightness of the first image and brightness of the second image.

5. An apparatus for inspecting a specimen, comprising:
a light source which emits a light;
an illuminator which illuminates a specimen, on which plural patterns are formed, with light emitted from the light sources;
an image capturing unit which captures a first image of a first area of the specimen in which patterns are formed, and a second image of a second area of the specimen in which patterns which are essentially the same with the patterns formed in the first area, are formed;
a pixel data creating unit which creates pixel data of the first image and corresponding pixel data of the second image, for each pixel;
a threshold determining unit which determines two thresholds for each pixel for detecting defects directly in accordance with the first image and the second image; and
defect detecting unit which detects defects on the specimen by processing said first image and the second image by using said two thresholds for each pixel,
wherein the thresholds are determined by using information of brightness of a local region of at least one of the first image and the second image, with the local region including an aimed pixel and peripheral pixels of the aimed pixel.

6. An apparatus for inspecting a specimen according to claim 5, wherein in said image capturing unit, said captured first image and said second image are both bright field images.

7. An apparatus for inspecting a specimen according to claim 5, wherein in said image capturing unit, said captured first image and said second image are both dark field images.

8. An apparatus for inspecting a specimen according to claim 5, wherein said pixel data creating unit creates said pixel data of the first image including brightness of the first image and said pixel data of the second image including brightness of the second image.

9. A method of inspecting a specimen, comprising:
illuminating a specimen, on which plural patterns are formed, with light emitted from a light source;
capturing a first bright field image of a first area of the specimen in which patterns are formed;
capturing a second bright field image of a second area of the specimen, in which patterns which are essentially the same with the patterns formed in the first area, are formed;
aligning the first bright field image and the second bright field image with an accuracy of less than one pixel unit;
creating data relating to pixels of the first image and corresponding pixels of the second image which are aligned with the accuracy of less than one pixel to match a brightness between the first bright field image and the second bright field image;
determining two thresholds for each pixel for detecting defects directly in accordance with the first image and the second image; and
detecting defects on the specimen by processing said first image and the second image by using said two thresholds for each pixel,
wherein the thresholds are determined by using information of brightness of a local region of at least one of the first image and the second image, with the local region including an aimed pixel and peripheral pixels of the aimed pixel.

10. A method of inspecting a specimen according to claim 9, wherein in the creating operation, the data relating to pixels of the first image including brightness of the first image and the data relating to pixels of the second image are both including brightness of the second image.

11. A method of inspecting a specimen according to claim 1, wherein regarding an extent of which pixels are used, the thresholds are determined by using information of brightness of only a local region of at least one of the first image and the second image, with the local region including only the aimed pixel and the peripheral pixels of the aimed pixel.

12. An apparatus for inspecting a specimen according to claim 5, wherein regarding an extent of which pixels are used, the thresholds are determined by using information of brightness of only a local region of at least one of the first image and the second image, with the local region including only the aimed pixel and the peripheral pixels of the aimed pixel.

13. A method of inspecting a specimen according to claim 9, wherein regarding an extent of which pixels are used, the thresholds are determined by using information of brightness of only a local region of at least one of the first image and the second image, with the local region including only the aimed pixel and the peripheral pixels of the aimed pixel.

14. A method of inspecting a specimen according to claim 1, wherein the creating, determining and detecting operations are conducted via pipeline-type image processing.

15. An apparatus for inspecting a specimen according to claim 5, wherein the pixel data creating unit, threshold determining unit and defect detecting unit operate via pipeline-type image processing.

16. A method of inspecting a specimen according to claim 9, wherein the creating, determining and detecting operations are conducted via pipeline-type image processing.

* * * * *